United States Patent
Nilsson

(10) Patent No.: US 12,200,445 B2
(45) Date of Patent: Jan. 14, 2025

(54) AUDITORY PROSTHESIS BATTERY AUTONOMY CONFIGURATION

(71) Applicant: Cochlear Limited, Macquarie University (AU)

(72) Inventor: Soren Nilsson, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 211 days.

(21) Appl. No.: 18/010,089

(22) PCT Filed: May 4, 2021

(86) PCT No.: PCT/IB2021/053712
§ 371 (c)(1),
(2) Date: Dec. 13, 2022

(87) PCT Pub. No.: WO2021/255537
PCT Pub. Date: Dec. 23, 2021

(65) Prior Publication Data
US 2023/0269545 A1    Aug. 24, 2023

Related U.S. Application Data

(60) Provisional application No. 63/043,245, filed on Jun. 24, 2020, provisional application No. 63/039,542, filed on Jun. 16, 2020.

(51) Int. Cl.
*H04R 25/00* (2006.01)
(52) U.S. Cl.
CPC .......... *H04R 25/305* (2013.01); *H04R 25/70* (2013.01)
(58) Field of Classification Search
None
See application file for complete search history.

(56) References Cited

U.S. PATENT DOCUMENTS

| 4,532,930 A | 8/1985 | Crosby et al. |
| 10,244,332 B2 | 3/2019 | Lineaweaver et al. |

(Continued)

FOREIGN PATENT DOCUMENTS

| KR | 10-2008-0074291 A | 8/2008 |
| WO | 2017103896 A1 | 6/2017 |

(Continued)

OTHER PUBLICATIONS

International Search Report and Written Opinion in counterpart International Application No. PCT/IB2021/053712, mailed Aug. 9, 2021, 7 pages.

*Primary Examiner* — Harry S Hong
(74) *Attorney, Agent, or Firm* — Edell, Shapiro & Finnan, LLC

(57) ABSTRACT

Presented herein are techniques for determining an estimated battery autonomy (e.g., estimated run-time) of a medical device having at least one actuator/transducer configured to mechanically stimulate a recipient. The medical device is specifically configured for the recipient and, as such, operates in accordance with a plurality of recipient-specific settings. The configuration of the medical device for the recipient (e.g., the plurality of recipient-specific settings), along with frequency and level current consumption characteristics of the medical device, are used to determine the estimated battery autonomy of the medical device. An environmental profile of the recipient can also be used with the configuration of the medical device for the recipient and the frequency and level current consumption characteristics of the medical device to determine the estimated battery autonomy.

26 Claims, 14 Drawing Sheets

(56) References Cited

U.S. PATENT DOCUMENTS

| | | |
|---|---|---|
| 2002/0076071 A1 | 6/2002 | Single |
| 2005/0143782 A1* | 6/2005 | Stessman .................. G01D 3/08 |
| | | 607/27 |
| 2006/0023907 A1* | 2/2006 | Kasztelan .............. H04R 25/00 |
| | | 381/317 |
| 2007/0179549 A1 | 8/2007 | Russie |
| 2008/0307243 A1 | 12/2008 | Lee |
| 2010/0114510 A1* | 5/2010 | Vaingast ............ G01R 31/3648 |
| | | 702/62 |
| 2012/0076334 A1* | 3/2012 | Anderson ............ H04R 25/505 |
| | | 381/317 |
| 2012/0197341 A1 | 8/2012 | Cowley et al. |
| 2012/0203484 A1* | 8/2012 | Ando .................. G01R 31/3832 |
| | | 702/63 |
| 2012/0326948 A1 | 12/2012 | Crocco et al. |
| 2013/0103114 A1 | 4/2013 | Single |
| 2014/0167656 A1 | 6/2014 | Yamada |
| 2015/0196759 A1 | 7/2015 | Meskens et al. |
| 2015/0196765 A1 | 7/2015 | Marnfeldt et al. |
| 2017/0127192 A1 | 5/2017 | Kuriger et al. |
| 2017/0215010 A1 | 7/2017 | Lineaweaver et al. |
| 2018/0221662 A1 | 8/2018 | Devcic |
| 2019/0339528 A1 | 11/2019 | Freeman et al. |

FOREIGN PATENT DOCUMENTS

| | | |
|---|---|---|
| WO | 2018146578 A1 | 8/2018 |
| WO | 2019-195866 A1 | 10/2019 |

\* cited by examiner

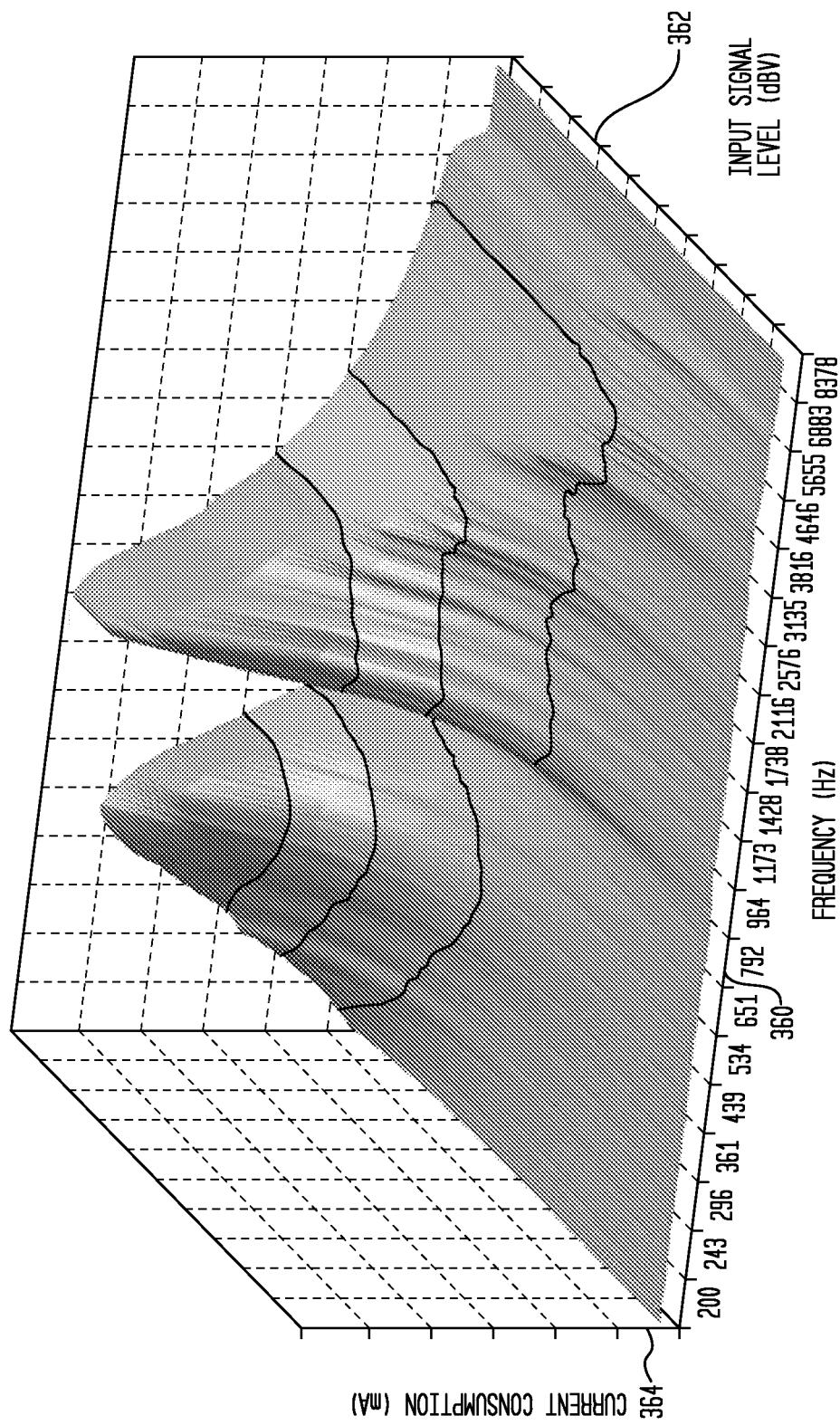

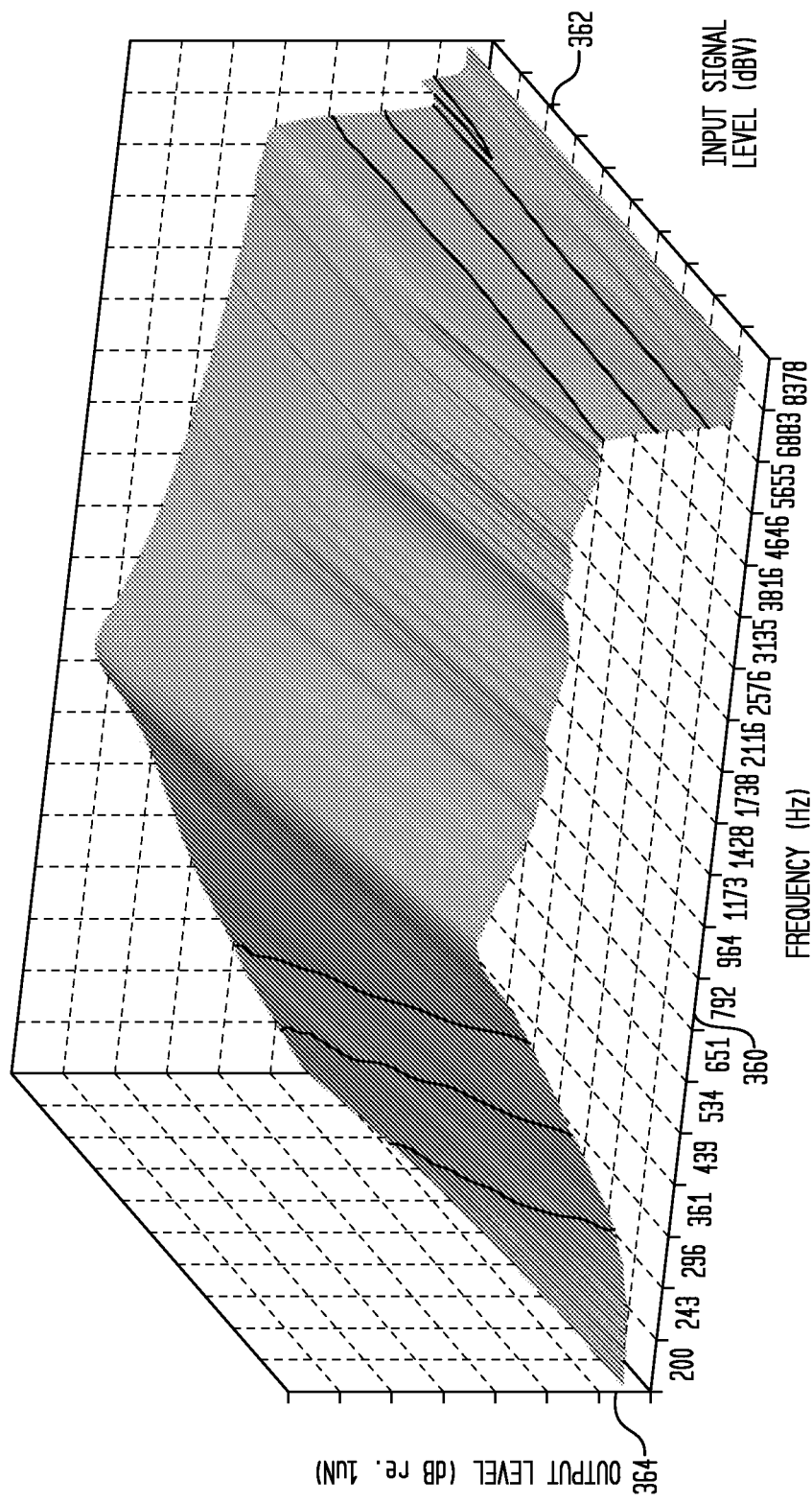

AUDITORY PROSTHESIS BATTERY AUTONOMY CONFIGURATION

BACKGROUND

Field of the Invention

The present invention relates generally to techniques for configuring a battery autonomy of an auditory prosthesis based on a recipient's hearing prescription.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: obtaining a hearing prescription associated with a recipient of a mechanically-stimulating auditory prosthesis, wherein the mechanically-stimulating auditory prosthesis is configured to be powered by at least one battery; and determining, based on the hearing prescription and a frequency-level current consumption of the mechanically-stimulating auditory prosthesis, an estimated battery autonomy of the mechanically-stimulating auditory prosthesis.

In another aspect, one or more non-transitory computer readable storage media are provided. The one or more non-transitory computer readable storage media comprise instructions that, when executed by at least one processor, are operable to: obtain a first set of operational settings of a battery-powered medical device having at least one actuator, wherein the first set of operational settings are determined based on characteristics of a recipient of the medical device; obtain data indicating at least a frequency-dependent current consumption of the at least one actuator; and predict, based on the data indicating the frequency-dependent current consumption of the at least one actuator, an estimated run-time of the medical device when operated in accordance with the first set of operational settings.

In another aspect, a computing device is provided. The computing device comprises: at least one interface for communication with a battery-powered auditory prosthesis, wherein the auditory prosthesis is configured to capture and convert sound signals into mechanical stimulation signals for delivery to a recipient; a memory; and one or more processors configured to: obtain a hearing prescription associated with the recipient of the auditory prosthesis, obtain data indicating a current consumption of the auditory prosthesis, wherein the auditory prosthesis has a current consumption that is dependent on attributes of the sound signals captured and converted into mechanical stimulation signals for delivery to the recipient, obtain a sound environment profile associated with the recipient of the auditory prosthesis, and determine an estimated battery autonomy for the auditory prosthesis based on the hearing prescription associated with the recipient, the data indicating a current consumption of the auditory prosthesis, and the sound environment profile associated with the recipient.

In another aspect, a method is provided. The method comprises: determining a first set of operational settings for a battery-powered auditory prosthesis comprising at least one actuator, wherein the first set of operational settings are determined based on characteristics of a recipient of the auditory prosthesis; obtaining data indicating at least a frequency-dependent current consumption of the auditory prosthesis; obtaining a sound environment profile associated with the recipient of the auditory prosthesis; and determining an estimated battery autonomy for the auditory prosthesis based on the first set of operational settings, the data indicating the frequency-dependent current consumption the auditory prosthesis, and the sound environment profile associated with the recipient.

BRIEF DESCRIPTION OF THE DRAWINGS

Embodiments of the present invention are described herein in conjunction with the accompanying drawings, in which:

FIG. 3A is a three-dimensional diagram illustrating the current consumed by an example bone conduction device as a function of both the frequency and level of input sound signals, in accordance with certain embodiments presented herein;

FIG. 3B is a three-dimensional diagram illustrating the output level by the example bone conduction device of FIG. 3A as a function of both the frequency and level of input sound signals, in accordance with certain embodiments presented herein;

DETAILED DESCRIPTION

Presented herein are techniques for determining an estimated battery autonomy (e.g., estimated run-time) of a medical device having at least one actuator/transducer configured to mechanically stimulate a recipient. The medical device is specifically configured for the recipient and, as such, operates in accordance with a plurality of recipient-specific settings. The configuration of the medical device for the recipient (e.g., the plurality of recipient-specific settings), along with current consumption characteristics of the medical device, are used to determine the estimated battery autonomy of the medical device. An environmental profile of the recipient can also be used with the configuration of the medical device for the recipient and the current consumption characteristics of the medical device to determine the estimated battery autonomy.

Merely for ease of description, the techniques presented herein are primarily described herein with reference to an example middle ear auditory prostheses (middle ear implant) and an example percutaneous bone conduction device. However, it is to be appreciated that the techniques presented herein may also be implemented with a variety of other devices/systems, including other medical devices/systems. For example, the techniques presented herein may be implemented with other auditory prostheses, including other bone conduction devices, hearing aids, other middle ear auditory prostheses, direct acoustic stimulators, electro-acoustic prostheses, cochlear implants, auditory brain stimulators, etc. The techniques presented herein may also be used with tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1A:
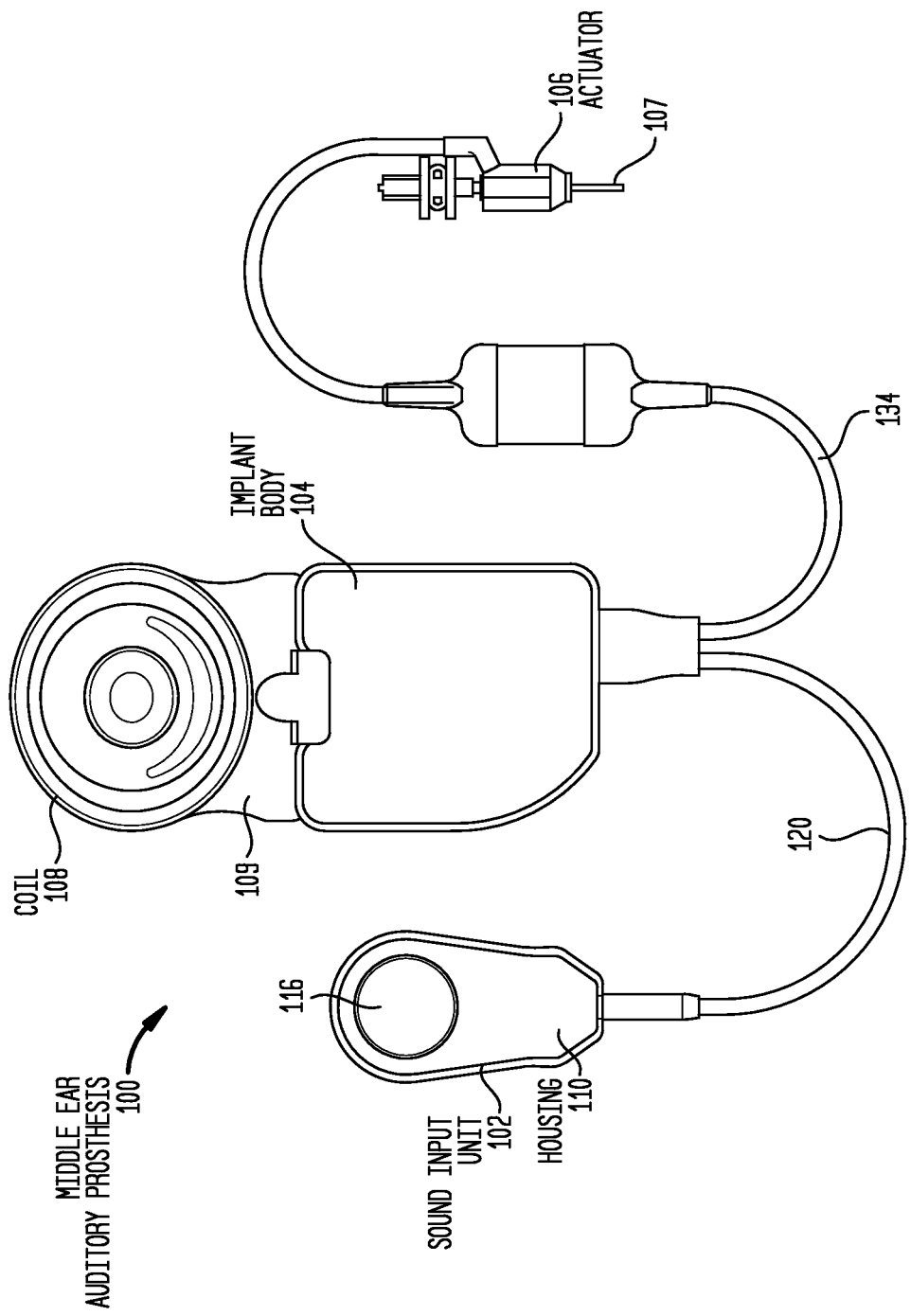
FIG. 1A is a top view of a totally implantable middle ear auditory prosthesis, with which certain embodiments presented herein may be implemented.
Figure 1B:
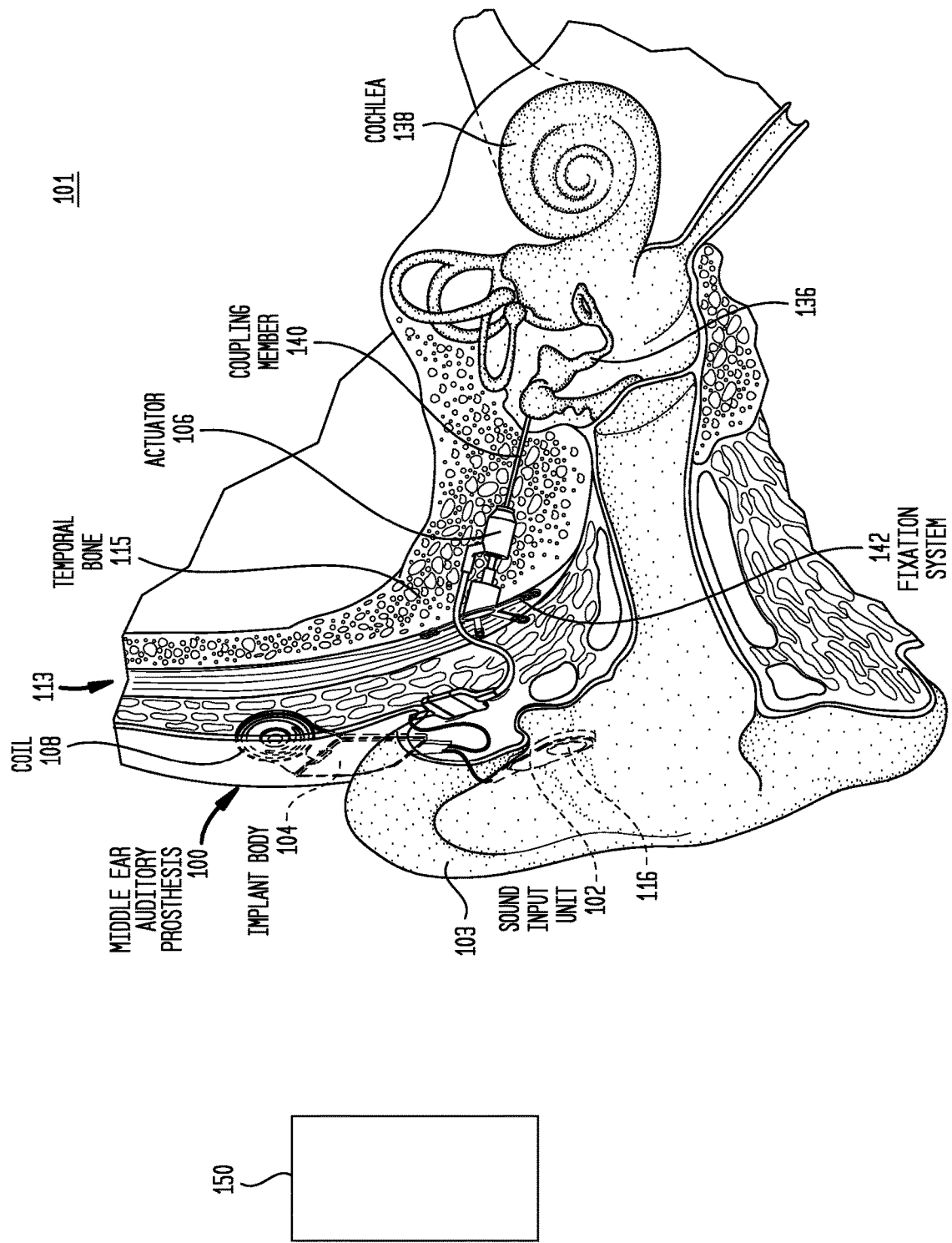
FIG. 1B is a schematic diagram illustrating the totally implantable middle ear auditory prosthesis of FIG. 1A.
Figure 1C:
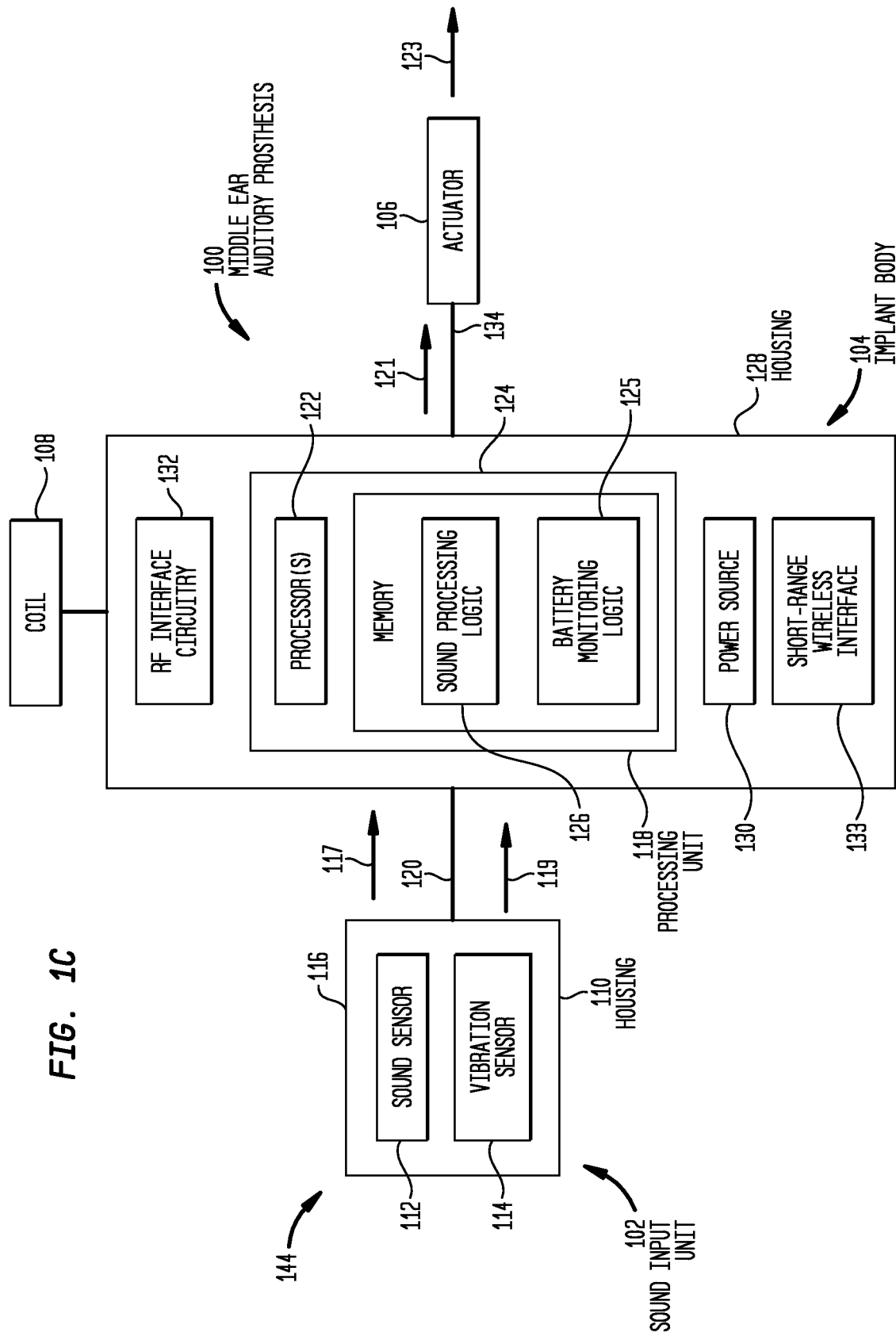
FIG. 1C is a block diagram of the totally implantable middle ear auditory prosthesis of FIG. 1A.

FIG. 1A is a top view of a totally implantable middle ear auditory prosthesis 100, in accordance with certain embodiments presented herein. FIG. 1B is schematic diagram illustrating the middle ear auditory prosthesis 100 of FIG. 1A implanted in a recipient 101, while FIG. 1C is a schematic block diagram of the middle ear auditory prosthesis 100. For ease of description, FIGS. 1A-1C will be described together.

A totally implantable medical device, such as middle ear auditory prosthesis 100, is a device in which all components of the device are configured to be implanted under tissue 113 (e.g., muscle tissue, epithelial tissue, nervous tissue, connective tissue, fat, bone tissue, etc.) of a recipient 101. Because all components are implantable, a totally implantable medical device operates, for at least a finite period of time, without the need of an external device. However, an external device, such as external device 150 shown in FIG. 1C, can operate with the totally implantable medical device.

An external device can be configured to, for example, provide power and/or data to the implantable medical device, receive data from the implantable device, etc.

The middle ear auditory prosthesis 100 of FIGS. 1A-1C comprises a sound input module/unit 102, an implant body 104, an actuator 106, and a coil 108, all implanted in the recipient 101. The sound input unit 102 comprises a substantially rigid housing 110, in which at least two implantable sensors 112 and 114 are disposed/positioned. The implantable sensor 112 is configured/designed to pick-up (capture) external acoustic sounds, while implantable sensor 114 is configured/designed to pick-up (capture) vibration caused, for example, by body noises. That is, the implantable sensor 112 is a "sound" sensor/transducer that is primarily configured to detect/receive external acoustic sounds, such as an implantable microphone, while the implantable sensor 114 is a "vibration" sensor that is primarily configured to detect/receive internal body noises and vibrations (e.g., vibrations caused by the action of an implantable actuator). The sound sensor 112 and the vibration sensor 114 are sometimes collectively referred to herein as "implantable auditory sensors" 144. As used herein, the actuator 106, sound sensor 112, and vibration sensor 114 are sometimes collectively referred to as "transducers" (i.e., the actuator 106, sound sensor 112, and vibration sensor 114, are each a device that converts variations in a physical quantity (energy) into an electrical signal, or vice versa).

The housing 110 is hermetically sealed and includes a diaphragm 116 that is proximate to the sound sensor 112. The diaphragm 116 may be unitary with the housing 110 and/or may be a separate element that is attached (e.g., welded) to the housing 110. The sound input unit 102 is configured to be implanted within the recipient 101. In one example shown in FIG. 1B, the sound input unit 102 is configured to be implanted within the skin/tissue adjacent to the outer ear 103 of the recipient. In this position, the diaphragm 116 is below the skin of the recipient that is close to the recipient's ear canal 105. In operation, sound signals that impinge on the skin adjacent to (i.e., on top of) the diaphragm 116 cause the skin adjacent the diaphragm 116, and thus the diaphragm 116 itself, to be displaced (vibrate) in response to the sound signals. The displacement of the diaphragm 116 is detected by the sound sensor 112. In this way, the sound sensor 112, although implanted within the recipient, is able to detect external acoustic sound signals (external acoustic sounds).

In the example of FIGS. 1A-1C, the sound sensor 112 and the vibration sensor 114 may each be electrically connected to the implant body 104 (e.g., in a separate casing connected to the main implant body 104). In operation, the sound sensor 112 and the vibration sensor 114 detect input (sound/vibration) signals (e.g., external acoustic sounds and/or body noises) and convert the detected input signals into electrical signals that are provided to the processing unit 118 (e.g., via lead 120). The processing unit 118 is configured to generate stimulation control signals 119 (FIG. 1C) based at least on the external acoustic sounds and/or the vibrations detected by the sound sensor 112 and/or the vibration sensor 114, respectively.

In the example of FIG. 1B, the processing unit 118 comprises at least one processor 122 and a memory device (memory) 124. The memory 124 may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The at least one processor 122 is, for example, a microprocessor or microcontroller that executes instructions for the logic stored in memory device 124. The processing unit 118 may be implemented, for example, on one or more printed circuit boards (PCBs).

In FIG. 1C, the memory 124 includes sound processing logic 126 and battery monitoring logic 125. The sound processing logic 126, when executed by the at least one processor 122, causes the at least one processor 122 to perform sound processing operations described herein (e.g., convert external acoustic sounds and/or the body noises detected by the sound sensor 112 and/or the vibration sensor 114 into stimulation control signals 119). As described further below, the battery monitoring logic 125, when executed by the at least one processor 122, causes the at least one processor 122 to monitor the discharge of a battery 130 in view of an estimated battery autonomy and, in certain examples, initiate one or more operations based on the battery monitoring.

It is to be appreciated that the arrangement for processing unit 118 in FIG. 1C is merely illustrative and that the techniques presented herein may be implemented with a number of different processing arrangements. For example, the sound processing unit 118 may be implemented with processing units formed by any of, or a combination of, one or more processors (e.g., one or more Digital Signal Processors (DSPs), one or more uC cores, etc.), firmware, software, etc. arranged to perform, for example, the operations described herein.

As shown, the implant body 114 includes a hermetically sealed housing 128 in which the processing unit 118 is disposed. Also disposed in the housing 128 is a rechargeable power source (e.g., rechargeable battery) 130 and communication and charging circuitry 132. The communication and charging circuitry 132 includes, for example, a closely-coupled transmitter/receiver (transceiver), sometimes referred to as or radio-frequency (RF) transceiver, and circuitry for recharging the at least one rechargeable battery 130.

Electrically connected to communication and charging circuitry 132 is the implantable coil 108, which is disposed outside of the housing 128. Implantable coil 108 is typically a wire antenna coil comprised of multiple turns of electrically insulated single-strand or multi-strand platinum or gold wire. The electrical insulation of implantable coil 108 is provided by a flexible molding (e.g., silicone molding) 109 (FIG. 1A). In general, the implantable coil 108 and the communication and charging circuitry 132 enable the receipt of power and data from an external device (such as external device 150) and, potentially, the transfer of data to an external device. However, it is to be appreciated that various types of energy transfer, such as infrared (IR), electromagnetic, capacitive and inductive transfer, may be used to transfer power and/or data from an external device and, as such, FIG. 1B illustrates only one example arrangement.

As noted, the communication and charging circuitry 132 and the implantable coil 108 enable the middle ear auditory prosthesis 100 to receive data/power from and/or transfer data to, an external device. That is, modulated signals transmitted bi-directionally through an inductive link (RF coil 108 and an external device) are used to support battery charging, device programming, status queries and user remote control. In certain examples, the external device may comprise an off-the-ear (OTE) unit. In other examples, the external device may comprise a behind-the-ear ear (BTE) unit or a micro-BTE unit, configured to be worn adjacent to the recipient's outer ear. Alternative external devices could comprise, for example, a device worn in the recipient's ear canal, a body-worn processor, a fitting system, a computing device, a pillow charger, a consumer electronic device (e.g., mobile phone communication), etc.

FIG. 1C has been described with reference to use of the communication and charging circuitry 132 and the implantable coil 108 for communication with an external device. However, in in certain embodiments, the implant body 104 may also include a short-range wireless interface 133 for communication with external devices. The short-range wireless interface 133 may be, for example, a Bluetooth® interface, Bluetooth® Low Energy (BLE) interface, or other interface making use of any number of standard or proprietary protocols. Bluetooth® is a registered trademark owned by the Bluetooth® SIG.

As noted above, the processing unit 118 generates stimulation control signals 119. The stimulation control signals 119 are provided to the actuator 106 (e.g., via lead 134) for use in delivering mechanical stimulation signals to the recipient 101. In FIG. 1C, the mechanical stimulation signals (vibration signals or vibration) delivered to the recipient are represented by arrow 121. Since the actuator 106 delivers mechanical stimulation signals to the recipient 101, the actuator 106 is sometimes referred to herein as a "mechanical stimulation arrangement." As such, the middle ear auditory prosthesis 100 is sometimes referred to herein as a type of "mechanically-stimulating auditory prosthesis." As noted, in the examples of FIGS. 1A-1C, the mechanical stimulation arrangement (actuator 106) is implanted in the recipient 101.

In the example of FIG. 1C, the actuator 106 delivers the vibration (mechanical stimulation signals) 121 to the recipient via the ossicular chain (ossicles) 136 (i.e., the bones of the middle ear, which comprise the malleus, the incus and the stapes). That is, the actuator 106 is physically coupled to the ossicles 136 via a coupling member 107 that moves (vibrations) in response to vibration of the actuator 106. The actuator 106 may be, for example, an electromagnetic or piezoelectric actuators with a frequency dependent power consumption.

Since the ossicles 136 are coupled to the oval window (not shown) of cochlea 138, vibration imparted to the ossicles 136 by the actuator 106 will, in turn, cause oval window to articulate (vibrate) in response thereto. Similar to the case with normal hearing, this vibration of the oval window sets up waves of fluid motion of the perilymph within cochlea 138 which, in turn, activates the hair cells inside of the cochlea 138. Activation of the hair cells causes appropriate nerve impulses to be generated and transferred through the spiral ganglion cells (not shown) and auditory nerve (not shown) to the brain (also not shown), where they are perceived as sounds.

It is to be appreciated that the arrangement shown in FIG. 1B in which the actuator 106 is mechanically coupled to the ossicles 136 is merely illustrative and that the techniques presented herein may be used with different mechanical stimulation arrangements. For example, in alternative embodiments, the actuator 106 could be coupled directly to the oval window, another opening in the cochlea 138 (e.g., a cochleostomy or the round window), an opening in the recipient's semicircular canals, the recipient's skull bone, etc.

Figure 2A:
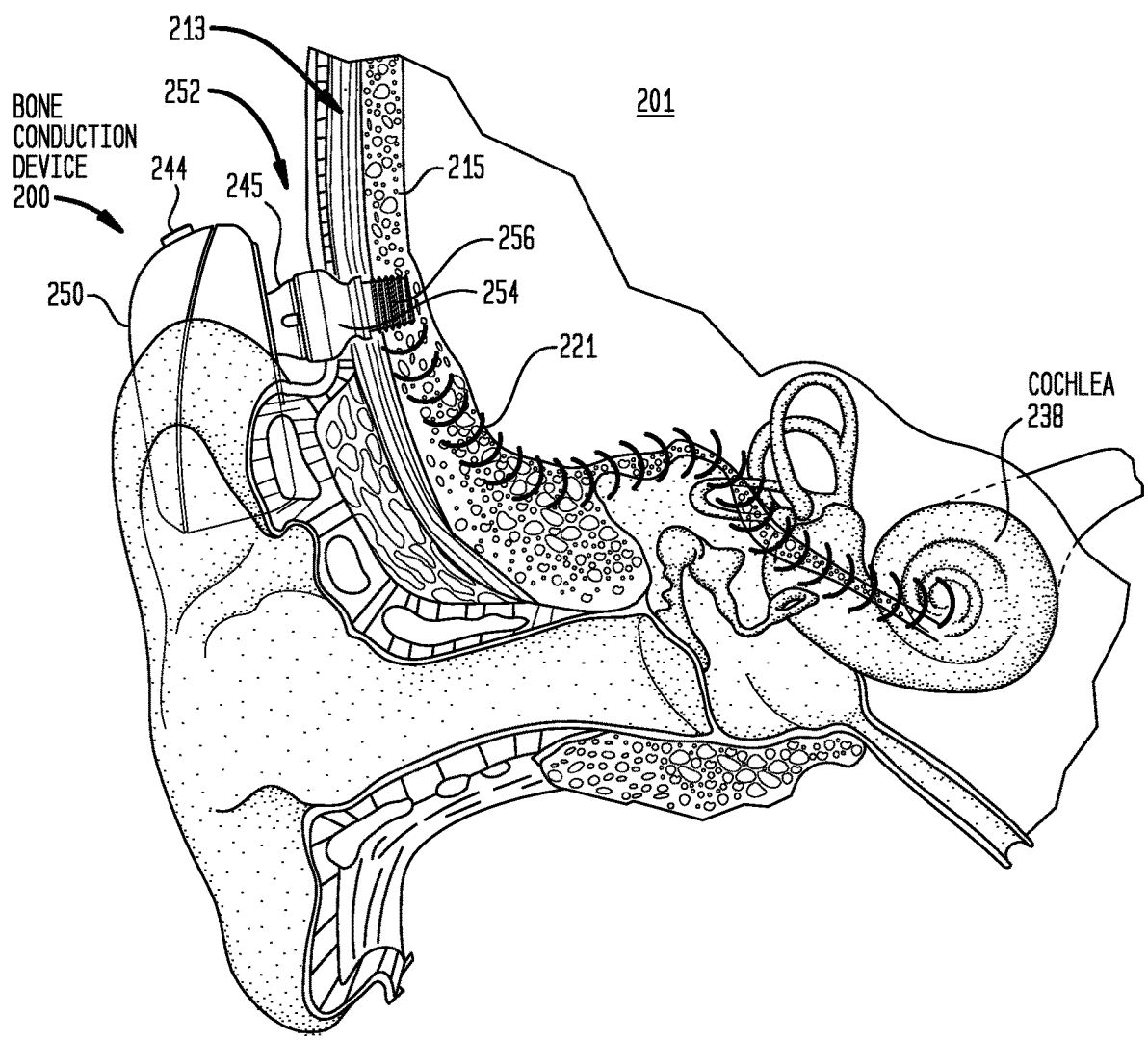
FIG. 2A is a perspective view of a percutaneous bone conduction device, with which certain embodiments presented herein may be implemented.
Figure 2B:
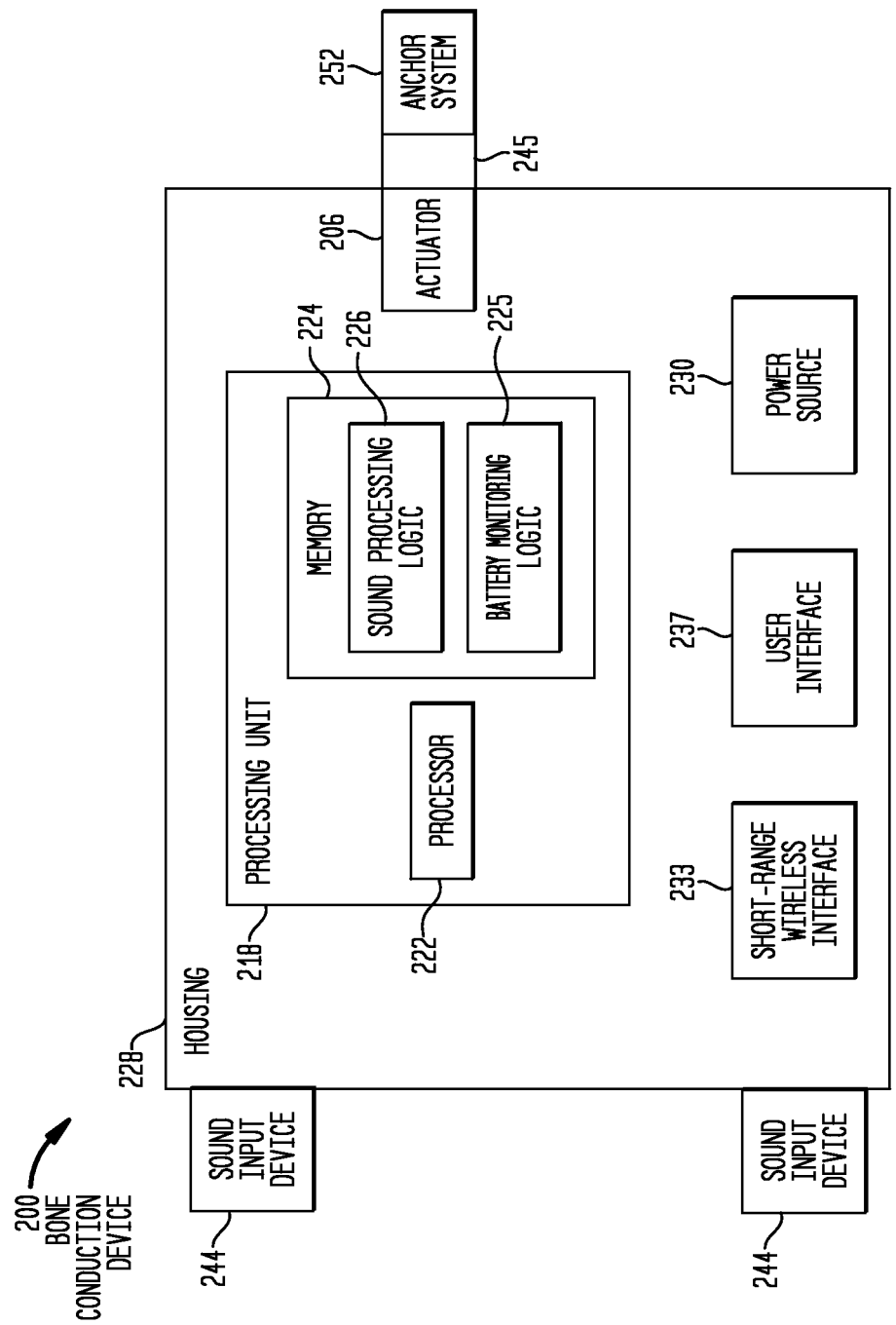
FIG. 2B is a functional block diagram of the percutaneous bone conduction device of FIG. 2A.

FIG. 2A is a perspective view of a percutaneous bone conduction device 200 that can be used with certain embodiments presented herein, while FIG. 2B is a schematic block diagram of the percutaneous bone conduction device 200. For ease of description, FIGS. 2A and 2B will be described together.

The percutaneous bone conduction device 200 is shown in FIG. 2A positioned behind outer ear 203 of the recipient. The bone conduction device 200 comprises a housing 248 in which a number of functional components are positioned and one or more sound input devices 244 configured to receive input signals, such as acoustic sound signals (sound signals). In the example of FIGS. 2A and 2B, the one or more sound input devices 244 comprise two microphones positioned on the housing 248. However, the sound input devices 244 can also or alternatively comprise, for example, a telecoil, an audio port, a Universal Serial Bus (USB) port, wireless input (e.g., wirelessly streamed sounds), etc. It is also to be appreciated that one or more of the sound input devices 244 can be located, for example, within the housing 248, on a cable extending from bone conduction device 200, etc.

As shown in FIG. 2B, the bone conduction device 200 also includes an actuator 206, a processing unit 218, at least one battery 230 (e.g., at least one rechargeable battery or at least one disposable battery), a short-range wireless interface 233, and a user interface 237.

The short-range wireless interface 233 may be, for example, a Bluetooth® interface, Bluetooth® Low Energy (BLE) interface, or other interface making use of any number of standard proprietary protocols. The user interface module 237 allows the recipient or other user to interact with bone conduction device 200. For example, user interface module 212 may allow the recipient to adjust the volume, alter the speech processing strategies, power on/off the device, etc. The user interface 212 may also or alternatively include an indicator, such as a Light Emitting Diode (LED), for status indication.

The processing unit 218 comprises at least one processor 222 and memory device (memory) 224. The memory 224 may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The at least one processor 222 is, for example, a microprocessor or microcontroller that executes instructions for the logic stored in memory 224. The processing unit 218 may be implemented, for example, on one or more printed circuit boards (PCBs).

The memory 224 includes sound processing logic 226 and battery monitoring logic 225, The sound processing logic 226, when executed by the at least one processor 222, cause the at least one processor 222 to perform sound processing operations described herein (e.g., convert external acoustic sounds detected by the sound input device(s) 244 into stimulation control signals). As described further below, the battery monitoring logic 225, when executed by the at least one processor 222, causes the at least one processor 222 to monitor the discharge of battery 230 in view of an estimated battery autonomy and, in certain examples, initiate one or more operations based on the battery monitoring.

It is to be appreciated that the arrangement for processing unit 218 in FIG. 2B is merely illustrative and that the techniques presented herein may be implemented with a number of different processing arrangements. For example, the sound processing unit 218 may be implemented with processing units formed by any of, or a combination of, one or more processors (e.g., one or more Digital Signal Processors (DSPs), one or more uC cores, etc.), firmware, software, etc. arranged to perform, for example, the operations described herein. In addition, the processing unit 218 may include charging circuitry for charging/recharging the power source 130 and circuitry for driving the actuator 206.

In operation, the processing unit 118 generates stimulation control signals based on input signals detected/captured by the sound input devices 244. The stimulation control signals are provided to the actuator 206 for use in delivering mechanical stimulation signals 221 to the recipient 201 via an anchor system (fixation system) 252 configured to be implanted in the recipient. In the example of FIGS. 2A and 2B, the anchor system 252 comprises percutaneous abutment 254 fixed to the recipient's skull bone 215 via a bone anchor (e.g., bone screw) 256. The percutaneous abutment 254 extends from skull bone 215 through tissue 213.

As shown, the bone conduction device 200 includes a coupling apparatus 245 that is configured to be attached to the percutaneous abutment 254. Attachment of the coupling apparatus 245 to the percutaneous abutment 254 forms a mechanical connection between the actuator 206 and the skull bone that facilitates efficient transmission of the mechanical stimulation signals 221 to the skull bone 215. When imparted to the skull bone 215, the mechanical stimulation signals 221 cause motion of the fluid within cochlea 238 of the recipient, which in turn induces a hearing sensation (i.e., enables the recipient to receive the sound signals received at the sound input devices 244). Since the actuator 206 delivers mechanical stimulation signals to the recipient 201, the actuator 206 is sometimes referred to herein as a "mechanical stimulation arrangement" and bone conduction device 200 is sometimes referred to herein as a type of "mechanically-stimulating auditory prosthesis." The actuator 206 may be, for example, an electromagnetic or piezoelectric actuators with a frequency dependent power consumption.

As noted above, middle ear auditory prosthesis 100 and percutaneous bone conduction device 200 include at least one battery 130 and 230, respectively, that provide operational power for other components of the respective device. However, the battery 130 and battery 230 will each only be able to provide a finite amount of power to the other components of the respective devices. Thereafter, the respective battery 130 or battery 230 will need to be replaced (e.g., in the case of disposable batteries) or recharged (e.g., in the case of integrated rechargeable batteries). Integrated (built-in) rechargeable batteries are used with implantable components, such as middle ear auditory prosthesis 100, while integrated rechargeable batteries are increasingly being used in external devices, such as percutaneous bone conduction device 200.

The total amount of energy a battery can store at any one time, often measured in terms of milliamp Hours (mAhs) or milli-watt hours (mWh), is referred to herein as the "capacity" of the battery. Reference to energy capacity in terms of mWH accounts for both the current and the battery voltage. When using mWh it is possible to equally compare batteries with different chemistries like Zinc-Air (up to 1.45 V) and Li-Ion (up to 4.2 V).

The capacity of a battery within a device generally dictates how long that device can operate before the battery needs to be recharged or replaced, which is sometimes referred to herein as the device "run-time" or the "battery autonomy." Therefore, the larger the battery capacity, the longer the battery autonomy (i.e., larger capacity batteries can generally power devices for longer periods of time). However, increased battery capacity requires increased battery sizes which, in turn, increases device size. As such, a tradeoff must be made between battery capacity and battery size (and corresponding device size). In addition, there is a general desire to make devices as small as possible, thus placing physical constraints on the battery size and, ultimately, the battery capacity.

For certain medical devices, such as cochlear implants and other electrically-stimulating prostheses, the current consumption thereof is relatively constant and is not dependent on the attributes of the input sound signals. Therefore, for electrically-stimulating prostheses, it is possible to measure the current draw/consumption of a particular electrically-stimulating prosthesis during a fitting/testing session and, consequently, calculate the battery autonomy for the electrically-stimulating auditory prosthesis therefrom. That is, the current measurement alone can be used to calculate the run-time of the electrically-stimulating auditory prosthesis, or rather how long the battery is likely to last before needing recharged.

However, for medical devices/prostheses with a mechanical stimulation arrangement (e.g., middle ear auditory prosthesis 100, percutaneous bone conduction device 200, hearing aids, etc.), sometimes referred to herein as "mechanically-stimulating prostheses," the current consumption/drain of the device (e.g., the actuator) is very dependent on the attributes of the sound signals received and processed by the mechanically-stimulating prostheses for stimulation of the recipient. The current consumption may be dependent on both the level (signal level or amplitude) of the sound signals and the frequency of the sound signals. As such, using conventional techniques, it is not possible to accurately estimate/predict the battery autonomy of a mechanically-stimulating prostheses.

Presented herein are techniques for estimating/predicting the battery autonomy of a particular mechanically-stimulating auditory prosthesis when the mechanically-stimulating auditory prosthesis is used by particular recipient. In particular, as described further below, the techniques presented herein estimate the battery autonomy of a mechanically-stimulating auditory prosthesis using the recipient's "hearing prescription" or "operational program/map" and, in certain embodiments, based on supplemental recipient data, such as an environmental profile of the recipient.

For ease of description, further details of the techniques presented herein are generally described with reference to bone conduction device 200 (FIGS. 2A and 2B) having a rechargeable battery 230. It is to be appreciated that reference to bone conduction device 200, and components thereof, is merely for purposes of illustration and that the techniques presented herein may be used with other types of implantable medical devices, such as middle ear auditory prosthesis 100, transcutaneous bone conduction devices, direct acoustic stimulators, hearing aids, etc.

As noted above, the current consumption of a mechanically-stimulating auditory prosthesis, such as bone conduction device 200, can be dependent on both the frequency and level of the input sound signals received (and processed) by the mechanically-stimulating auditory prosthesis. This current consumption dependency on sound frequency and sound level is generally shown in FIG. 3A.

More specifically, FIG. 3A is a three-dimensional graph/diagram illustrating the current consumed by an example bone conduction device 200 as a function of both the frequency and level of input sound signals that are received, processed, and converted to mechanical stimulation signals by the bone conduction device 200. That is, FIG. 3A includes a first axis 360 illustrating the frequency of input sound signals in Hertz (Hz) and a second axis 362 illustrating the input signal level in voltage decibel (dBV). In addition, FIG. 3A includes a third axis 364 illustrating the current consumption of the example bone conduction device 200 in milliamps (mA) as a function of the frequency 360 and the signal level 362. As shown, in the example of FIG. 3A, the lower frequency sounds will drain/consume more current than higher frequency (except for a band around the resonance of the actuator) and high sound levels will drain more current than low sound levels.

FIG. 3B is a three-dimensional graph/diagram illustrating the output level by the example bone conduction device 200 of FIG. 3A as a function of both the frequency and level of input sound signals. That is, FIG. 3B includes a first axis 360 illustrating the frequency of input sound signals in Hertz (Hz) and a second axis 362 illustrating the input signal level in voltage decibel (dBV). In addition, FIG. 3B includes a third axis 366 illustrating the output level of the example bone conduction device 200 in decibels relative to 1 micro Newton (dB, re: 1 µN) as a function of the frequency 360 and the signal level 362. As shown, in the example of FIG. 3B, the lower frequency sounds will drain/consume more current than higher frequency (except for a band around the resonance of the actuator) and high sound levels will drain more current than low sound levels.

FIG. 3A illustrates a reduction in the current consumed around 800 Hz. The reason for this reduction is that this is the resonant frequency of the actuator 206 within bone conduction device 200, making the actuator 206 most efficient at that frequency. Similarly, while current consumption is very low around 800 Hz, FIG. 3B illustrates that the output level is the strongest at the same frequency (800 Hz), again due to the resonant frequency of the underlying actuator 206.

FIGS. 3A and 3B generally illustrate that, in order to be able to predict/estimate the battery autonomy for bone conduction device 200 (or another mechanically-stimulating auditory prosthesis), the operation of device itself needs to be characterized as a function of both sound level and sound frequency (e.g., determine current consumption as a function of sound level and sound frequency). The current consumption of the bone conduction device 200 (or another mechanically-stimulating auditory prosthesis) as a function of both sound level and sound frequency is sometimes referred to herein as the "frequency-level current consumption" of the bone conduction device 200.

Unlike electrically-stimulating hearing prostheses, the frequency-level current consumption of a mechanically-stimulating auditory prosthesis, alone, is insufficient to be able to determine the estimated battery autonomy of that prosthesis when used by a particular recipient. Instead, as described below, the estimated battery autonomy is also based on the operational settings of the prosthesis for a given recipient.

More specifically, different recipients of bone conduction device 200 can have different types and/or levels of hearing loss (e.g., two recipients may have different levels of hearing in the lower frequency ranges, etc.). As a result, the effectiveness of mechanically-stimulating auditory prostheses, and other auditory prostheses, generally depends on how well a particular prosthesis is configured for, or "fitted" to, the specific recipient of the particular prosthesis. For instance, the "fitting" of an auditory prosthesis to a specific recipient, sometimes also referred to as "programming" or "mapping," creates a set of recipient-specific operational settings (collectively and generally referred to as the recipient's "hearing prescription" or "operational program/map") that define the specific operational characteristics of the hearing prosthesis to convert sound signals into mechanical stimulation for delivery to the recipient. In the case of a mechanically-stimulating auditory prostheses, fitting determines, among other parameters, the frequency-dependent gain settings of the prosthesis (e.g., the gain used to drive the actuator at each of a number of frequency bands/regions). That is, since the recipient's hearing loss may not be the same across all frequencies, different gain may be utilized to drive the actuator (e.g., to amplify sound signals) at different frequency bands/regions. Other settings that can impact current consumption may include, for example, the applied sound compression (e.g., how much the sound is compressed in the sound processing unit), LED settings, wireless streaming capabilities, wireless interface power amplification, or other settings that can affect current consumption of the device. For example, with high sound compression, loud sounds are damped and low sounds are amplified. In general, more sound compression results in lower current consumption. As such, the amount of compression applied could be increased in order to reduce current consumption.

Since different recipients can have different types and/or levels of hearing loss, different recipients of the bone conduction device 200 can have different hearing prescriptions (e.g., the operational settings of the device that are set based on the recipient's hearing loss). As such, the hearing prescription of the recipient of bone conduction device 200 (or other mechanically-stimulating auditory prosthesis) is sometimes referred to herein as the "recipient-specific hearing prescription."

In accordance with certain embodiments presented herein, the recipient-specific hearing prescription associated with the recipient 201 of bone conduction device 200, along with the frequency-level current consumption of the bone conduction device 200, can be used to estimate/predict the battery autonomy of rechargeable battery 230. However, in certain embodiments, the estimated/predicted battery autonomy can also be based on data/information indicating/characterizing the recipient's typical "sound environment profile" or "environmental profile." As used herein, a recipient's sound environment profile is information indicating the types of sound environment(s) to which the recipient is exposed and, in certain embodiments, one or more quantification metrics indicating the recipient's expose to the different sound environments (e.g., data indicating the time spent in each environment, ratios, etc.). The sound environment profile can include, for example, the recipient's age, hobbies, living situation, family details, occupation, etc.

Accurately estimating/predicting the battery autonomy of a mechanically-stimulating auditory prosthesis, such as bone conduction device 200, is important to ensure that the battery autonomy is sufficient to generally operate the device for a single day. That is, it is generally desired that a new disposable battery provide a recipient with at least one full day of operation (i.e., a new disposable battery should power the bone conduction device for at least approximately 14-16 hours without the need to replace the battery). Similarly, it is generally assumed that a recipient has the ability to charge his/her rechargeable battery at night and, as such, the goal is to provide a recipient with approximately one full day of operation on a single battery charge (i.e., a fully charged battery should power the bone conduction device for at least approximately 14-16 hours without the need to recharge the battery).

For certain recipients, the estimated battery autonomy determined in accordance with the techniques presented herein may be insufficient to operate the device for a single day. In such embodiments, the hearing prescription associated with the recipient (i.e., one or more settings of the bone conduction device 200) may be adjusted/altered so as to reduce the current consumption of the device and, accordingly, increase the battery autonomy so as to ensure the recipient will not lose hearing before the end of the day. For example, if the battery autonomy is too short, the frequency-dependent gain settings, sound compression, etc. of the bone conduction device 200 can be adjusted. In certain such embodiments, the gain that is applied in certain frequency bands/regions that drain extra current (e.g., low frequencies), but which are less important for speech recognition, may be reduced. This reduction could be applied to all or a subset of sound environments.

Conversely, for certain recipients, the estimated battery autonomy may be significantly more that is needed to operate the bone conduction device 200 for a single day. In such embodiments, one or more settings of the bone conduction device 200 may be adjusted/altered so as to reduce the battery capacity (e.g., change the termination voltage of the battery 230). In general, higher capacity batteries have shorter cycle lives than lower capacity batteries. By decreasing the battery capacity, the cycle life of the integrated rechargeable battery 230 can be increased.

Figure 4:
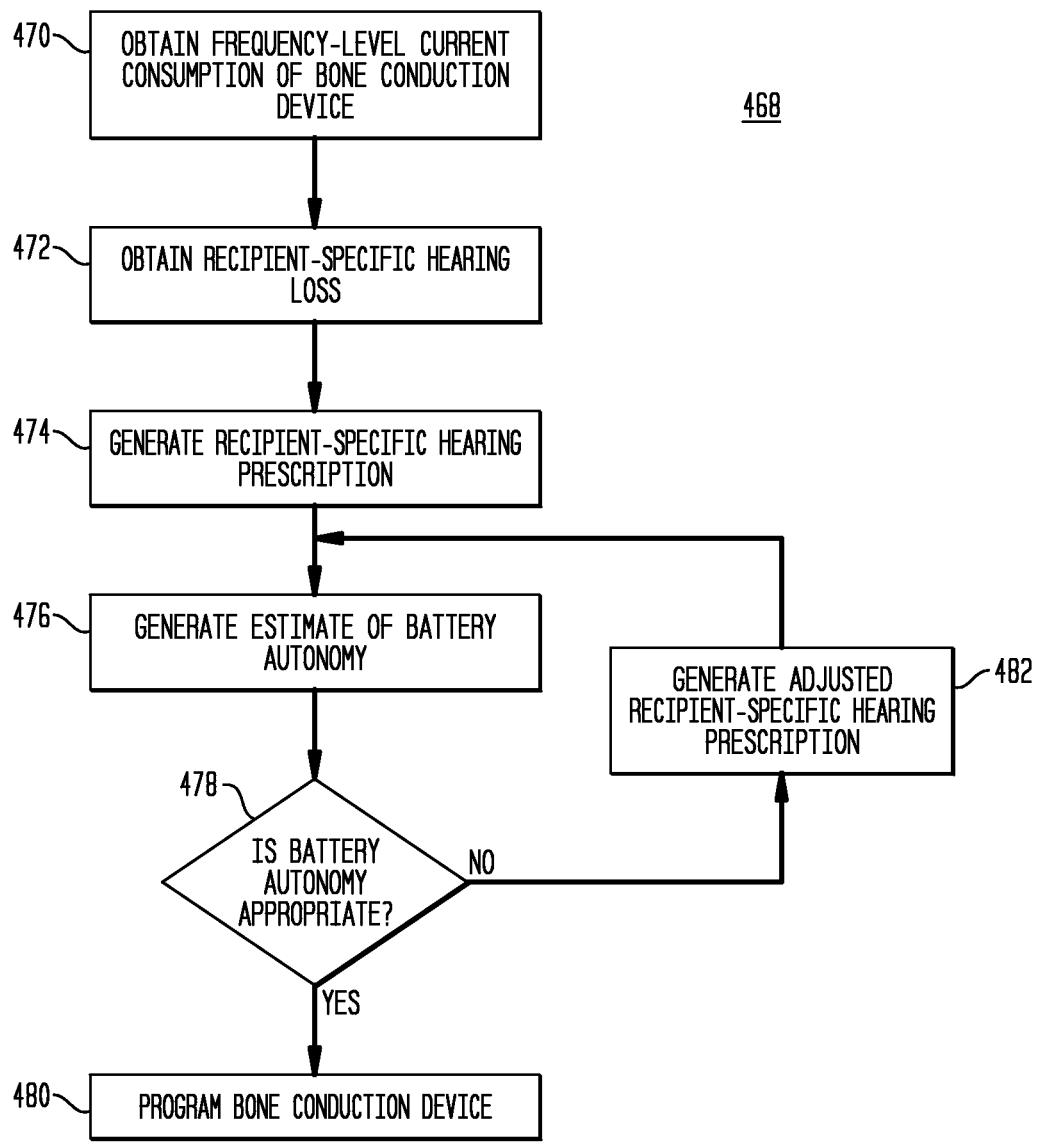
FIG. 4 is a detailed flowchart of an example method, in accordance with certain embodiments presented herein.

FIG. 4 is a detailed flowchart a method 468 illustrating aspects of the techniques presented herein. Again, for ease of illustration, method 468 will be described with reference to bone conduction device 200 of FIGS. 2A and 2B.

Method 468 begins at 470 where a computing device (e.g., computer, mobile device, fitting system, etc.) obtains the frequency-level current consumption of the bone conduction device 200. That is, the computing device obtains data indicating the current consumed by the bone conduction device 200 when processing sound signals of different levels and frequencies. In certain embodiments, the data indicating the current consumed by the bone conduction device 200 could be obtained from the bone conduction device itself (e.g., the device measures current internally) or from another device. For example, a measuring device could be configured determine the output force of the bone conduction device 200 and this data can be used to determine the current consumed by the bone conduction device 200 when processing sound signals of different levels and frequencies.

At 472, the computing device obtains data representing the hearing loss of the specific recipient 201, referred to herein as the recipient-specific hearing loss (hearing loss relative to frequency). The recipient-specific hearing loss could be determined by the computing device (e.g., during a fitting session), obtained from the recipient's clinical records (e.g., determined through prior measurement), etc. In certain embodiments, the recipient-specific hearing loss may be represented by an audiogram of one or both ears of the recipient 201. An audiogram is a graph illustrating audible threshold for standardized frequencies as measured by an audiometer (e.g., a graphic representation of the relationship of sound frequency and the minimum sound intensity for hearing).

At 474, the recipient-specific hearing loss is used to generate/determine the recipient-specific hearing prescription associated with the recipient of bone conduction device 200. As noted above, the recipient-specific hearing prescription refers to the collection of operational settings of the bone conduction device 200 that are set based on the recipient's hearing loss. Also as noted above, the hearing prescription may include, for example, the frequency-dependent gain settings of the bone conduction device 200 used to generate mechanical stimulation signals for delivery to the recipient.

At 476, the computing device generates an estimate/prediction of the battery autonomy for rechargeable battery 230 based at least on the recipient-specific hearing prescription and the frequency-level current consumption of the bone conduction device 200. That is, the recipient-specific hearing prescription and the frequency-level current consumption are used to generate an estimate of the run-time of the bone conduction device 200, when bone conduction device 200 is operated in accordance with the recipient-specific hearing prescription. Further details regarding generation of the estimate of the battery autonomy are provided below with reference to FIG. 5.

Returning to FIG. 4, at 478, a determination is made as to whether the estimated battery autonomy is appropriate/suitable for the recipient. In general, the determination of whether the estimated battery autonomy is appropriate for the recipient can take a number of different forms and can determine, for example, whether the battery autonomy is too short and/or too long. A determination that the battery autonomy is too short means that the battery autonomy is likely insufficient to power the bone conduction device 200 for a single day (e.g., at least 16 hours). A determination that the battery autonomy is too long means that the battery autonomy is significantly greater than is needed to power the bone conduction device 200 for a single day.

In certain examples, the operations at 478 may include one or more comparisons of the estimated battery autonomy to one or more threshold time levels. For example, the operations at 478 may include comparison of the estimated battery autonomy to a minimum battery autonomy threshold (e.g., 16 hours) and/or a comparison of the estimated battery autonomy to a maximum battery autonomy threshold (e.g., 24 hours). If the estimated battery autonomy is below the maximum battery autonomy threshold and above the minimum battery autonomy threshold, then the estimated battery autonomy is appropriate.

Stated more generally, the determination at 478 can include a determination of whether the estimated battery autonomy is greater than at least a first time threshold. In further embodiments, the determination at 478 can include a determination of whether the estimated battery autonomy is greater than at least a first time threshold and less than at least a second time threshold.

In the example of FIG. 4, if, at 478, the estimated battery autonomy is determined to be appropriate for the recipient, then method 468 proceeds to 480 where the bone conduction device 200 is programmed/configured with the recipient-specific hearing prescription. That is, at 480, the recipient-specific hearing prescription is instantiated in the bone conduction device 200 for subsequent use by the recipient. However, if, at 478, the estimated battery autonomy is determined to be inappropriate for the recipient, then method 468 proceeds to 482. At 482, the computing device generates an adjusted recipient-specific hearing prescription based on the results of the determination of whether estimated battery autonomy is appropriate and, in certain embodiments, based on one or more inputs from a user (e.g., audiologist).

The generation of the adjusted recipient-specific hearing prescription can depend on whether the estimated battery autonomy is determined (at 478) to be too short or two long. For example, if the estimated battery autonomy is determined to be too short, then the recipient-specific hearing prescription can be adjusted in a manner that reduces the current/power consumption of the bone conduction device 200. In certain such embodiments, the frequency-dependent gain settings used to drive the actuator 206 to generate mechanical stimulation signals can be adjusted in certain frequency regions. In the same or other embodiments, certain features of the bone conduction device 200 could be disabled, the applied sound compression could be adjusted, etc. If the estimated battery autonomy is determined to be too long, then the capacity of the rechargeable battery 230 could be reduced (e.g., change the termination voltage of the battery). It is noted that a recipient with initial low current needs may receive a reduced charge termination voltage, but there may be a need in the future to have that reduction removed or adjusted if the current demands of the device change.

After the adjusted recipient-specific hearing prescription is generated, the method 468 returns to 476 where the adjusted recipient-specific hearing prescription and the frequency-level current consumption of the bone conduction device 200 are used to generate an updated estimate of the battery autonomy (updated estimated battery autonomy). This updated estimated battery autonomy is analyzed at 478 to determine whether the updated estimated battery autonomy is appropriate for the recipient, in the similar manner as described above.

Again, if the updated estimate of the battery autonomy is appropriate, then the method ends at 480 where the bone conduction device 200 is programmed/configured with the adjusted recipient-specific hearing prescription. Otherwise, the method 468 returns to 482 for generation of another adjusted recipient-specific hearing prescription. The operations of 482, 476, and 478 are repeated until an updated estimate of the battery autonomy is determined to be appropriate and, accordingly, the bone conduction device 200 is programmed at 480 with the corresponding adjusted recipient-specific hearing prescription. In certain examples, several iterations of 482, 476, and 478 may be needed before an acceptable battery autonomy is reached.

It is to be appreciated that method 468 is merely illustrative and that the various operations can be performed in different combinations and/or orders. For example, in certain embodiments, the battery autonomy estimation could be generated with the recipient-specific hearing prescription (e.g., combine 476 with 474 and 482). In such embodiments, the estimated battery autonomy, or data relating thereto, could be displayed to a user (e.g., audiologist) in real-time via display screen of the computing device. The user could, for example, see the estimated battery autonomy updated on the screen, again in real-time, as the recipient-specific hearing prescription is adjusted by the computing device (e.g., in response to user inputs). For example, the user could change the frequency-dependent gain settings of the bone conduction 200 and the computing device could determine and display the resulting updated estimated battery autonomy in real-time. In this way, the need to loop through 476, 478, and 482 could be eliminated.

Figure 5:
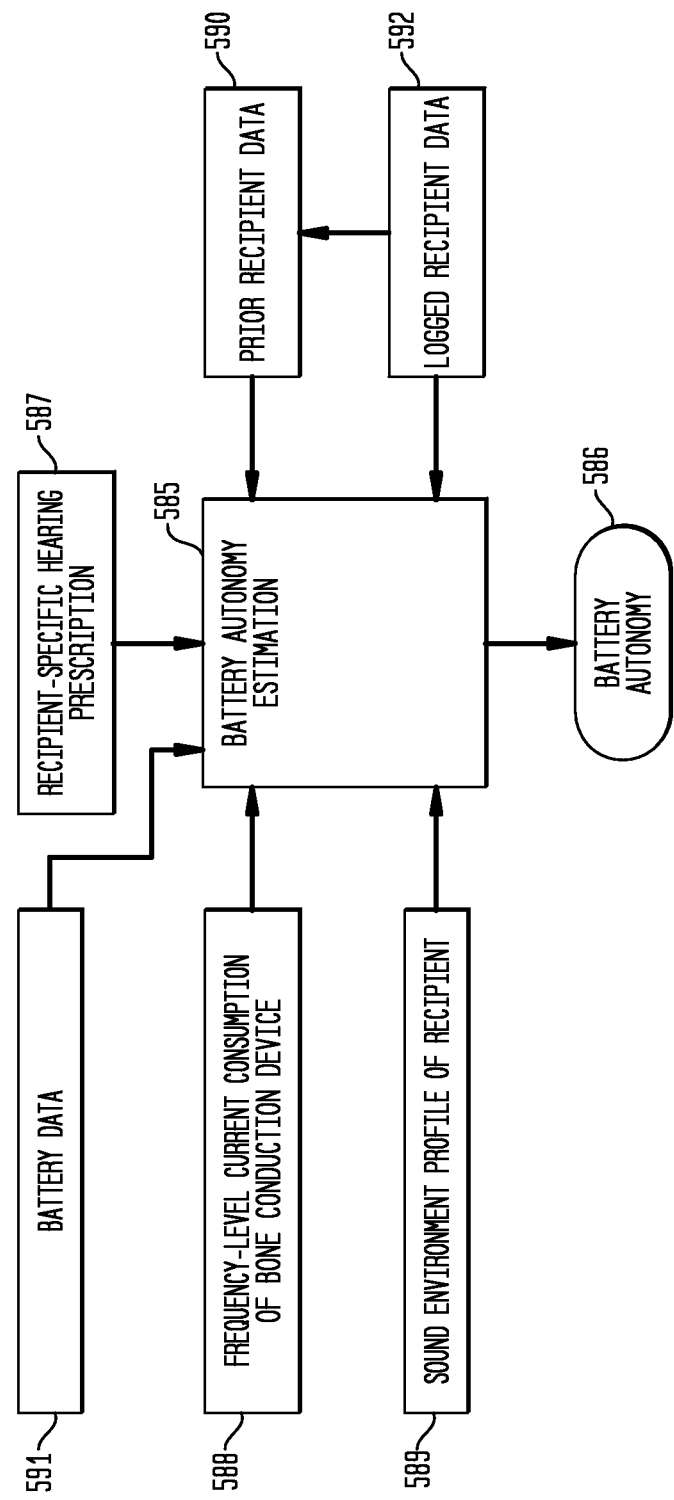
FIG. 5 is a diagram illustrating further details of a battery autonomy estimation process, in accordance with certain embodiments presented herein.

As noted above, FIG. 5 is a schematic diagram illustrating further details regarding the generation/determination of an estimated battery autonomy, in accordance with certain embodiments presented herein. In particular, FIG. 5 illustrates the different input data that may be used to generate the estimated battery autonomy. The generation/determination of an estimated battery autonomy is generally represented in FIG. 5 by block 585 and the resulting estimated battery autonomy is generally represented in FIG. 5 by block 586.

As shown in FIG. 5, the estimated battery autonomy 586 can be generated based on a number of different pieces of input data from a number of different sources. In particular, as noted above, the estimated battery autonomy 586 is generated based at least on the recipient-specific hearing prescription and the frequency-level current consumption of the bone conduction device 200. In FIG. 5, the recipient-specific hearing prescription is represented by block 587 and the frequency-level current consumption of the bone conduction device 200 is represented by block 588.

The frequency-level current consumption 588 (current characterization) can be, for example, determined during design and development of the bone conduction device, during device manufacture, etc. The current consumption can be measured in many different ways, including at different frequencies, different signal levels, and with sound files representing different sound environments.

As shown in FIG. 5, in certain embodiments, the estimated battery autonomy 586 can also be generated based on the recipient's "sound environment profile." In FIG. 5, the recipient's sound environment profile is represented by block 589. As noted above, a recipient's sound environment profile is personal data/information that can be used to estimate the types of sound environments to which the recipient is exposed on a daily basis and, in certain embodiments, the recipient's expose to those sound environments on a daily basis (e.g., how often the recipient is likely exposed to a particular sound environment, how long each day the recipient is likely to be in a particular sound environment, etc.). The sound environment profile can include, for example, the recipient's age, gender, hobbies, ethnicity, living situation, family details, occupation, etc.

For example, the sound environment profile of a school age child may indicate that she will generally spend 7 hours a day in school (e.g., listening to lectures, conversing with fellow students, etc.), 1 hour each day watching streaming videos, 1 hour each day engaged in sports, and the remainder of the data in a home environment with siblings. In contrast, the sound environment profile of an elderly person may indicate that she will spend 1-2 hours watching television, 1-2 hours in conversation, and the rest of the day in relative quiet. In general, the various different pieces of information about a recipient's daily routine can be used to generate the sound environment profile. In addition, greater amounts of information about the recipient's daily routine will result in a more accurate sound environment profile and, ultimately, a more accurate estimated battery autonomy.

In certain embodiments, the estimated battery autonomy 586 can also be generated based on battery data 591. The battery data 591 may include, for example, the, battery capacity, cycle life (e.g., number of complete charge/discharge cycles that the battery is able to support before the capacity of the battery falls below some threshold of its original capacity so as be insufficient for its intended purpose), etc. For a new device, the battery capacity or cycle life may be known from the battery manufacturer. However, if a battery has been in use for some period of time (e.g., in a refitting situation), the battery capacity or cycle life may have to be estimated or calculated in some manner. For example, if a recipient had a low current need during the first fitting, then the battery capacity could have been intentionally reduced via a reduced charge termination voltage, in order to gain more charge cycles. When the recipient returns for a refitting (maybe via remote fitting), there may be a need to increase that charge termination voltage again. The battery capacity or cycle life could each be estimated or calculated in a number of different manners. For example, certain embodiments may determine the number of "battery days" for the bone conduction device (e.g., number of days the battery has been in use) and analyze that date in view of manufacturer data to determine the current battery capacity or cycle life. It may also be possible to track the number of charge/discharge cycles and directly calculate the remaining capacity, life cycle, battery health, etc.

In certain embodiments, the estimated battery autonomy 586 can also be generated based on the logged data obtained from other recipients. In FIG. 5, the logged data obtained from other recipients is represented by block 590 and is referred to as "prior recipient data." More specifically, certain medical devices, such as bone conduction device 200, can be configured to collect (log) data as the medical device is used by a recipient. The resulting logged data may include, for example, data relating to the recipient's sound environments and metrics indicating the recipient's exposure to various sound environments on a daily basis. This logged data can be coupled with data about the recipient (e.g., hearing prescription, age, hobbies, occupation etc.) to form the prior recipient data 590. The prior recipient data 590 can be de-personalized (e.g., scrubbed of recipient identifying data) and stored in a database of prior recipient data that can be used in fitting other recipients with a similar hearing prescription and/or a similar sound environment profile.

A database of prior recipient data, formed from data from many recipients, would be created over time and, ultimately, analyzed during the battery autonomy estimation process 585. In these embodiments, the analysis of prior recipient data 590 from other recipients with similar hearing prescriptions and/or a similar sound environment profiles, it is possible to better predict what sound environments a recipient will be exposed to on a daily basis, which accordingly improves the accuracy of the estimated battery autonomy 596. The more recipients that have similar profiles, the better the prediction of the estimated battery autonomy 596. This type of data may be important, for example, when fitting a new recipient with bone conduction device 200 for the first time.

Finally, in certain embodiments, the estimated battery autonomy 586 can also be generated based on the logged data obtained from the specific recipient's use of bone conduction device 200 (i.e., the recipient's own logged data). In FIG. 5, the logged data obtained from the recipient's use of use of bone conduction device 200 is represented by block 592 and is referred to as "logged recipient data." That is, when the recipient is allowed to use the bone conduction device 200, the bone conduction device 200 can record data (e.g., statistics) indicating what sound environments, sound levels, etc. the specific recipient has been exposed to on a daily basis (e.g., data relating to the recipient's sound environments and exposure to various sound environments since a previous fitting session). This data can include the types of sound environments, time spent in each environment, sound levels, sound frequencies, features, etc. The logging of the recipient data could be implemented as part of the battery monitoring logic 225.

The logged recipient data 592 may be used, for example, when a recipient returns to an audiologist following one or more previous/prior fitting sessions. For example, if the recipient returns to the audiologist for a refitting, the logged recipient data 592 represents the actual sound environments that the recipient has been exposed to on a regular basis. Therefore, the logged recipient data 592 can be used to generate/determine a refined sound environment profile for the recipient which, in turn, can be used to re-estimate the battery autonomy at 585. The use of the refined sound environment profile data could enable an even more precise estimation of the battery autonomy 586. As noted, this data can be de-personalized (e.g., scrubbed of recipient identifying data) and put into a database for use in fitting other recipients with a similar profile.

In the example of FIG. 5, if one, two, three, etc. of the different types of input data are available (e.g., 588, 589, 590, 591, and/or 592), the different input data can be added into the battery autonomy estimation 585 with different weights. For example, the sound environment profile 589 may be weighted in one manner, while the prior recipient data 590 (e.g., logged data from other recipients) can be weighted in another manner. The logged recipient data 592 may be weighted with a relative higher importance that the prior recipient data 590.

In general, accuracy of a battery autonomy estimation/prediction for a mechanically-stimulating auditory prosthesis, such as bone conduction device 200, will depend on the actual sound environments experienced by the recipient. As such, it may not be possible, to predict exactly how long time the battery will last on any given day, particularly if the recipient is exposed to unexpected sound environments or to sound conditions that are different form the sound environment profile. In general, some days the battery will last less for shorter periods of time, while other days the battery may last for longer periods of time. As such, a mechanically-stimulating auditory prosthesis in accordance with embodiments presented herein, such as bone conduction device 200, can include additional battery support functionality, such as an advanced low battery warning system, or specialized programs for different situations. For example, the device could be prepared during fitting with a special low current program that can be used when the recipient knows that he/she will need an operation device for an extended period of time (e.g., during travel, staying up all night watching Olympic games from the other side of the globe, etc.).

In certain such embodiments, the advanced low battery warning system, which could be implemented as part of the battery monitoring logic 225, is aware of the initial estimated battery autonomy and is configured to monitor the discharge of the battery 230 (e.g., dynamically determine/estimate the remaining battery autonomy throughout the day). That is, the bone conduction device 200 could include functionality that is aware of the estimated battery autonomy, and which is configured to monitor the discharge of the battery 230. In this way, the bone conduction device 200 can warn the recipient (or a parent or caregiver) when, for example, the remaining battery autonomy is below a threshold level, when the battery is being discharged too quickly, etc.

Although as described as part of bone conduction device 200, the battery support functionality could also be built into an external device (e.g., a smartphone application) operating with the bone conduction device 200. In such embodiments, the external device could receive data from bone conduction device 200 for use in monitoring the battery 230. In any case, the bone conduction device 200 and/or the external device could enable the recipient or other user to take one or more actions to increase the remaining battery autonomy (e.g., temporarily adjust gain settings at certain frequencies).

Figure 6:
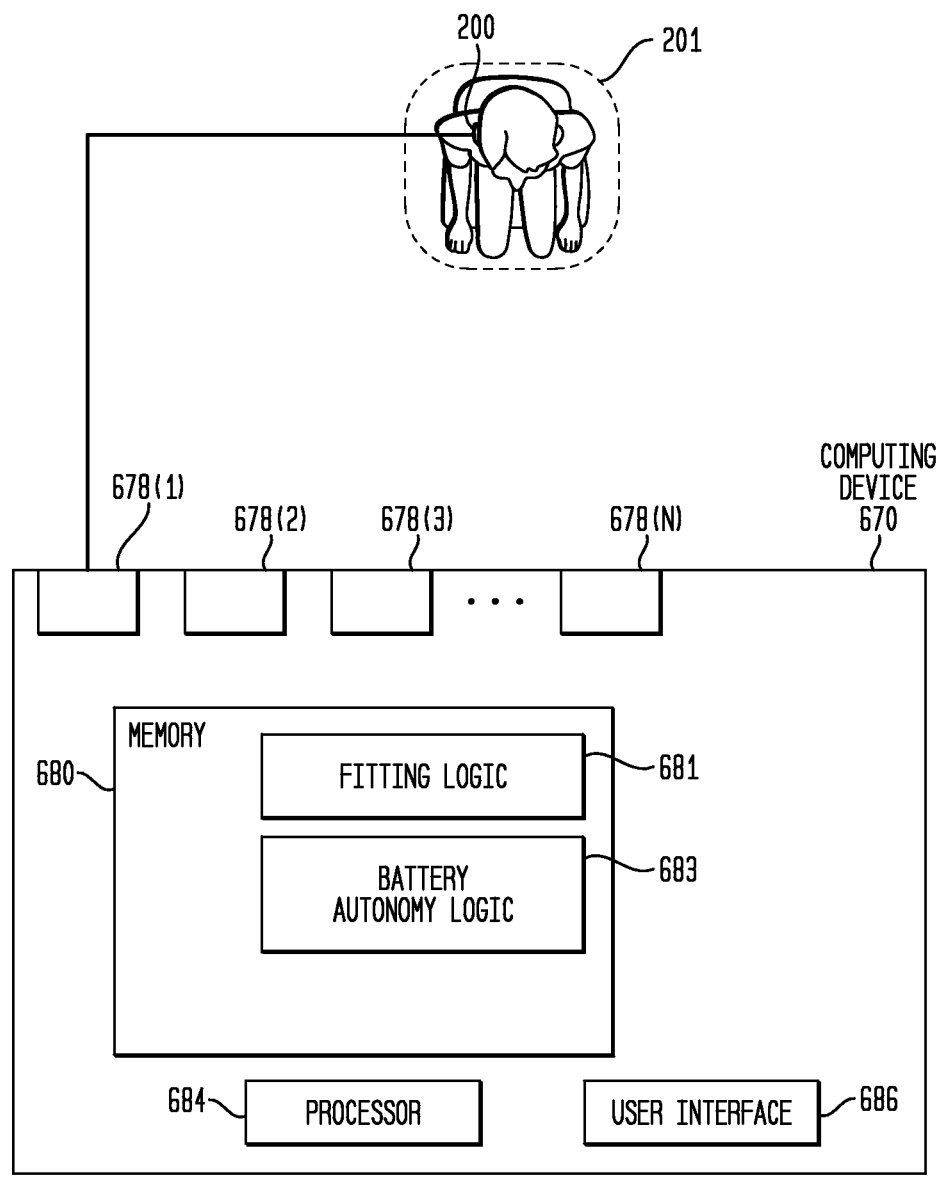
FIG. 6 is a block diagram of a computing device, in accordance with certain embodiments presented herein.

As noted above, in certain embodiments, the estimated battery autonomy can be determined at a computing device (e.g., desktop computer, laptop computer, tablet computer, mobile phone, fitting system, etc.). FIG. 6 illustrates one example computing device 670 that can be used to determine a recipient's estimated battery autonomy, in accordance with certain embodiments presented herein. As shown, computing device 670 comprises a plurality of interfaces/ports 678(1)-678(N), a memory device (memory) 680, at least one processor 684, and a user interface 686.

The interfaces 678(1)-678(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 6, interface 678(1) is connected to bone conduction device 200. Interface 678(1) may be directly connected to the bone conduction device 200 and may be configured to communicate with bone conduction device 200 via a wired or wireless connection (e.g., telemetry, Bluetooth, etc.).

The user interface 686 includes one or more output devices, such as a liquid crystal display (LCD) and a speaker, for presentation of visual or audible information to a clinician, audiologist, or other user. The user interface 686 may also comprise one or more input devices that include, for example, a keypad, keyboard, mouse, touchscreen, etc.

The memory 680 comprises fitting logic 681 and battery autonomy logic 683. The memory 680 may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The at least one processor 122 is, for example, a microprocessor or microcontroller that executes instructions for the logic stored in memory device 124. The processing unit 118 may be implemented, for example, on one or more printed circuit boards (PCBs).

The at least one processor 684 is, for example, a microprocessor or microcontroller that executes instructions for the fitting logic 681 and the battery autonomy logic 683. Thus, in general, the memory 680 may comprise one or more tangible (non-transitory) computer readable storage media (e.g., a memory device) encoded with software comprising computer executable instructions and when the software is executed (by the processor 684) it is operable to perform the techniques described herein.

As noted above, FIGS. 1A-1C and 2A-2B illustrate two suitable configurations of medical devices that can implement the techniques described herein. It is to be appreciated that these two arrangements are illustrative, and that the techniques described herein can be implemented in any of a variety of other medical device configurations and/or other contexts. For example, embodiments of the techniques presented herein may be used with other auditory prostheses, including other bone conduction devices, other middle ear prostheses, direct acoustic stimulators, electro-acoustic prostheses, hearing aids, cochlear implants, auditory brain stimulators, etc. The techniques presented herein may also be used with tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 7:
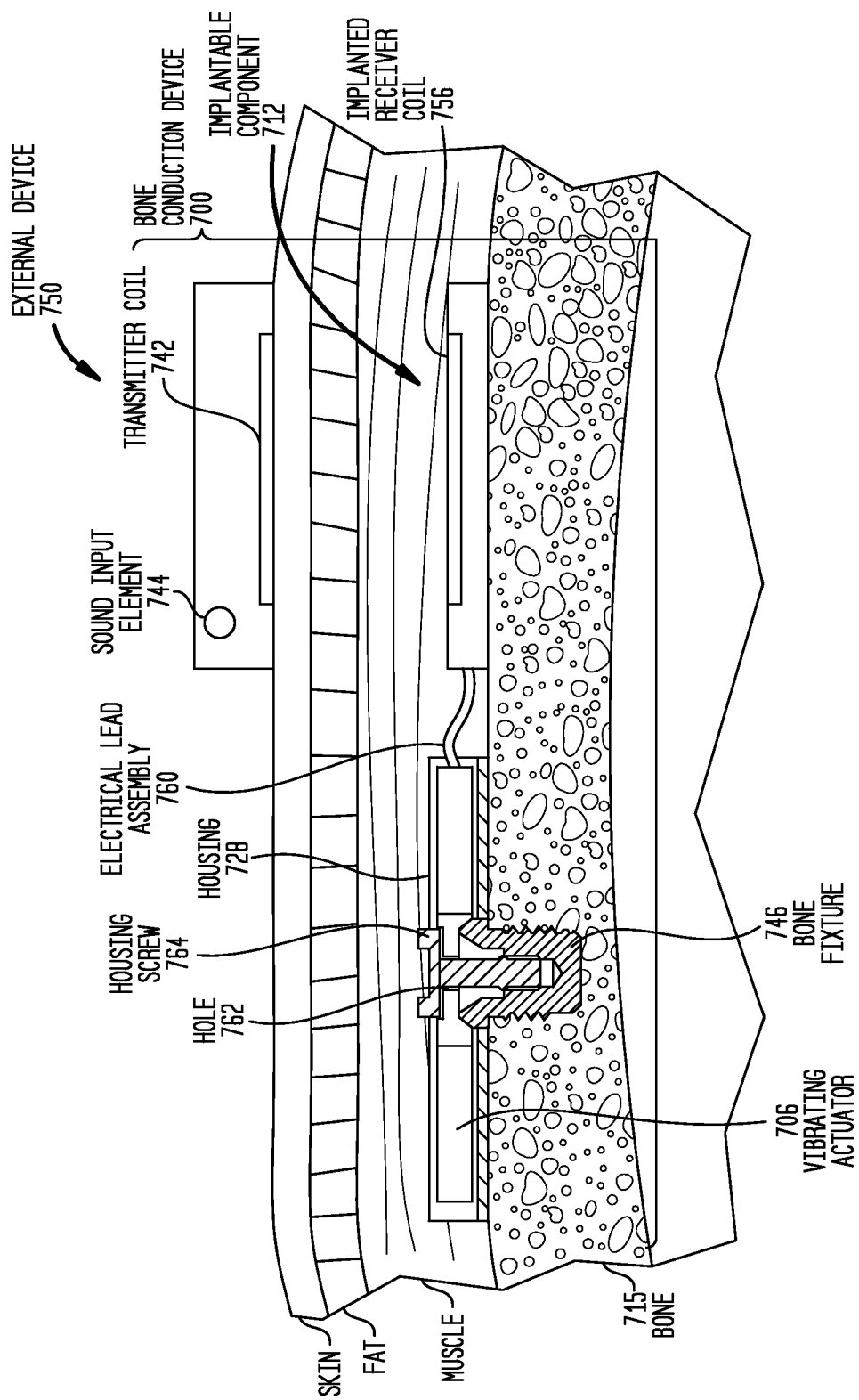
FIG. 7 is a schematic diagram illustrating an active transcutaneous bone conduction device, with which certain embodiments presented herein may be implemented.

For example, FIG. 7 is a schematic diagram illustrating an exemplary transcutaneous bone conduction device 700 with which certain embodiments presented herein be implemented. The transcutaneous bone conduction system 700 includes an external device/component 750 and an implantable component 712. The transcutaneous bone conduction device 700 is an active transcutaneous bone conduction device, meaning that the mechanical stimulation arrangement (e.g., actuator 706) is located in the implantable component 712. Specifically, the actuator 706 is located in housing 728 of the implantable component 712.

External device 750 includes one or more sound input devices 744 that convert sound into electrical signals. Specifically, the transcutaneous bone conduction device 700 provides these electrical signals to actuator 706, or to a sound processor (not shown) that processes the electrical signals, and then provides those processed signals to the implantable component 712 through the skin of the recipient via a magnetic inductance link. In this regard, a transmitter coil 742 of the external device 750 transmits these signals to implanted receiver coil 756 located in the implantable component 712. Components (not shown) in a housing 728, such as, for example, a signal generator or an implanted sound processor, then generate electrical signals to be delivered to the actuator 706 via electrical lead assembly 760. The actuator 706 converts the electrical signals into vibrations.

The actuator 706 is mechanically coupled to the housing 728. The housing 728 is substantially rigidly attached to bone fixture 746. In this regard, housing 728 includes a through hole 762 that is contoured to the outer contours of the bone fixture 746. Housing screw 764 is used to secure housing 728 to bone fixture 746. In this way, the actuator 706 is able to deliver mechanical stimulation signals to the skull bone 715 of the recipient.

Figure 8:
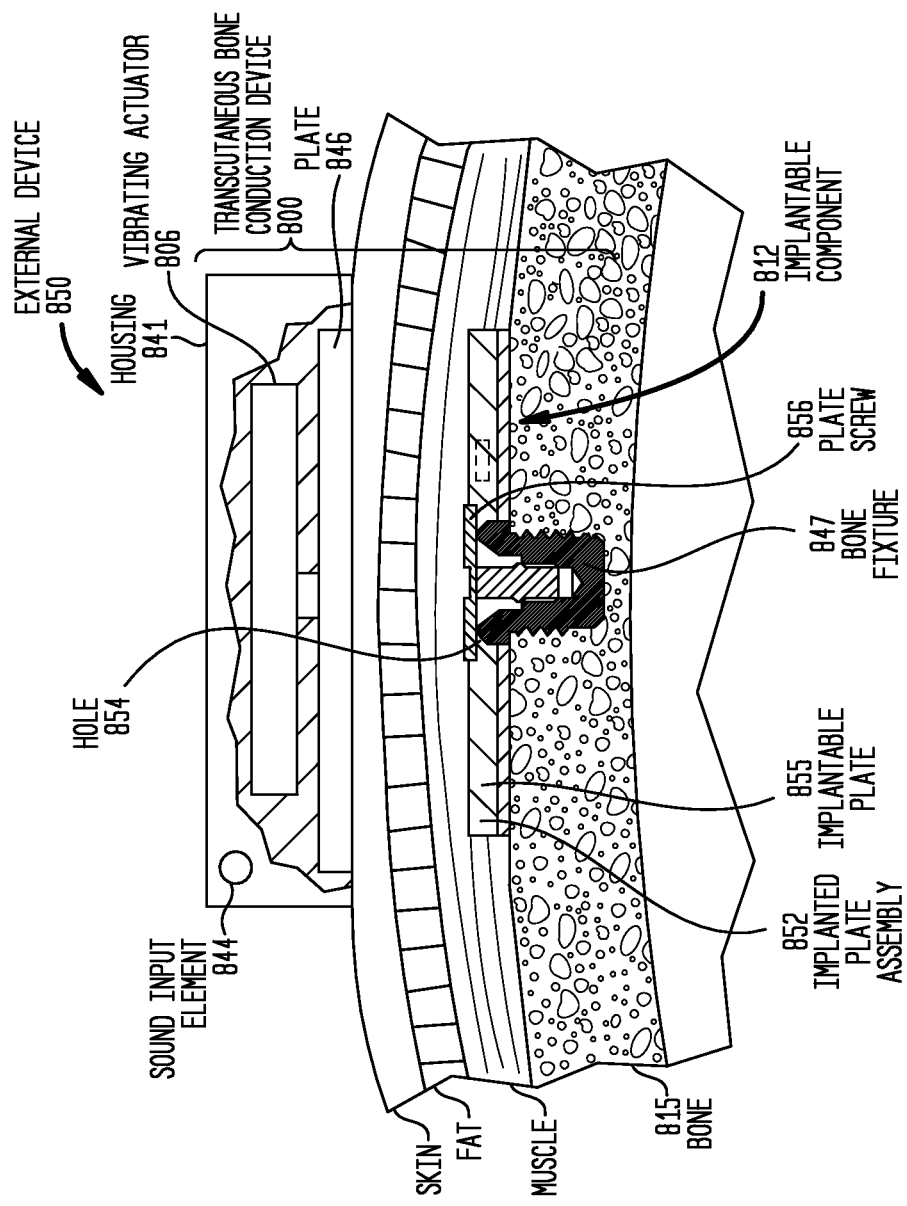
FIG. 8 is a schematic diagram illustrating a passive transcutaneous bone conduction device, with which certain embodiments presented herein may be implemented.

FIG. 8 depicts an exemplary embodiment of a transcutaneous bone conduction device 800 with which embodiments presented here may be implemented. In this example, transcutaneous bone conduction device 800 comprises an external device/component 850 and an implantable component 812 implanted under the tissue (e.g., skin, fat, muscle) of the recipient. The transcutaneous bone conduction device 800 of FIG. 8 is a passive transcutaneous bone conduction device, meaning the actuator 806 is located in the external device 850 (i.e., not implanted in the recipient).

More specifically, actuator 806 is located in housing 841 of the external component, and is coupled to plate 846. Plate 846 may be in the form of a permanent magnet and/or in another form that generates and/or is reactive to a magnetic field, or otherwise permits the establishment of magnetic attraction between the external device 850 and the implantable component 812 sufficient to hold the external device 850 against the skin of the recipient.

In an exemplary embodiment, the vibrating actuator 806 is a device that converts electrical signals into vibration. In operation, one or more sound input elements 844 converts sound signals into electrical signals. Specifically, the transcutaneous bone conduction device 800 provides these electrical signals to the actuator 806, or to a sound processor (not shown) that processes the electrical signals, and then provides those processed signals to the actuator 806. The actuator 806 converts the electrical signals (processed or unprocessed) into vibrations. Because actuator 806 is mechanically coupled to plate 846, the vibrations are transferred from the actuator 806 to plate 846. Implanted plate assembly 852 is part of the implantable component 812, and is made of a ferromagnetic material that, in certain embodiments, may be in the form of a permanent magnet, that generates and/or is reactive to a magnetic field, or otherwise permits the establishment of a magnetic attraction between the external device 850 and the implantable component 812 sufficient to hold the external device 850 against the skin of the recipient. Accordingly, vibrations produced by the actuator 706 are transferred from plate 846 across the skin to plate 855 of plate assembly 852. This may be accomplished as a result of mechanical conduction of the vibrations through the skin, resulting from the external device 850 being in direct contact with the skin and/or from the magnetic field between the two plates. These vibrations are transferred without penetrating the skin with a solid object such as an abutment as detailed above with respect to a percutaneous bone conduction device.

As may be seen, the implanted plate assembly 852 is substantially rigidly attached to bone fixture 847 in this embodiment. In this regard, implantable plate assembly 852 includes through hole 854 that is contoured to the outer contours of the bone fixture 847. This through hole 854 thus forms a bone fixture interface section that is contoured to the exposed section of the bone fixture 847. In an exemplary embodiment, the sections are sized and dimensioned such that at least a slip fit or an interference fit exists with respect to the sections. Plate screw 856 is used to secure plate assembly 852 to bone fixture 847. As can be seen in FIG. 8, the head of the plate screw 856 is larger than the hole through the implantable plate assembly 852, and thus the plate screw 856 positively retains the implantable plate assembly 852 to the bone fixture 847.

The above embodiments have generally been described with reference to auditory prostheses that directly mechanically stimulate a recipient with vibration (e.g., physical pathway between the actuator and the recipient's body). However, as noted above, the techniques may also be implemented in hearing aids or other auditory prosthesis that indirectly mechanically stimulate a recipient with acoustic stimulation signals. In particular, certain hearing aids include an actuator in the form of a "receiver" that emits acoustic signals that stimulate the recipient via the ear drum, ossicular chain, etc. In such embodiments, the actuator (receiver) has a frequency dependent (and possibly level dependent) current consumption. Therefore, as used herein, the term "mechanically-stimulating auditory prostheses" include acoustic hearing aids and the term "actuator" includes receivers of such acoustic hearing aids.

Figure 9:
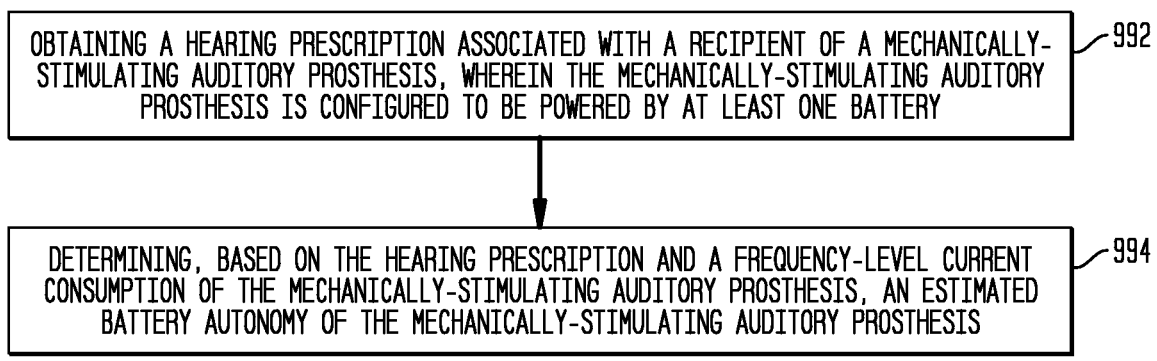
FIG. 9 is a flowchart of an method, in accordance with certain embodiments presented herein.

FIG. 9 is a flowchart of a method 990 in accordance with certain embodiments presented herein. Method 990 begins at 992 where a computing device obtains a hearing prescription associated with a recipient of a mechanically-stimulating auditory prosthesis, where the mechanically-stimulating auditory prosthesis is configured to be powered by at least one battery. At 994, the computing device determines, based on the hearing prescription and a frequency-level current consumption of the mechanically-stimulating auditory prosthesis, an estimated battery autonomy of the mechanically-stimulating auditory prosthesis.

Figure 10:
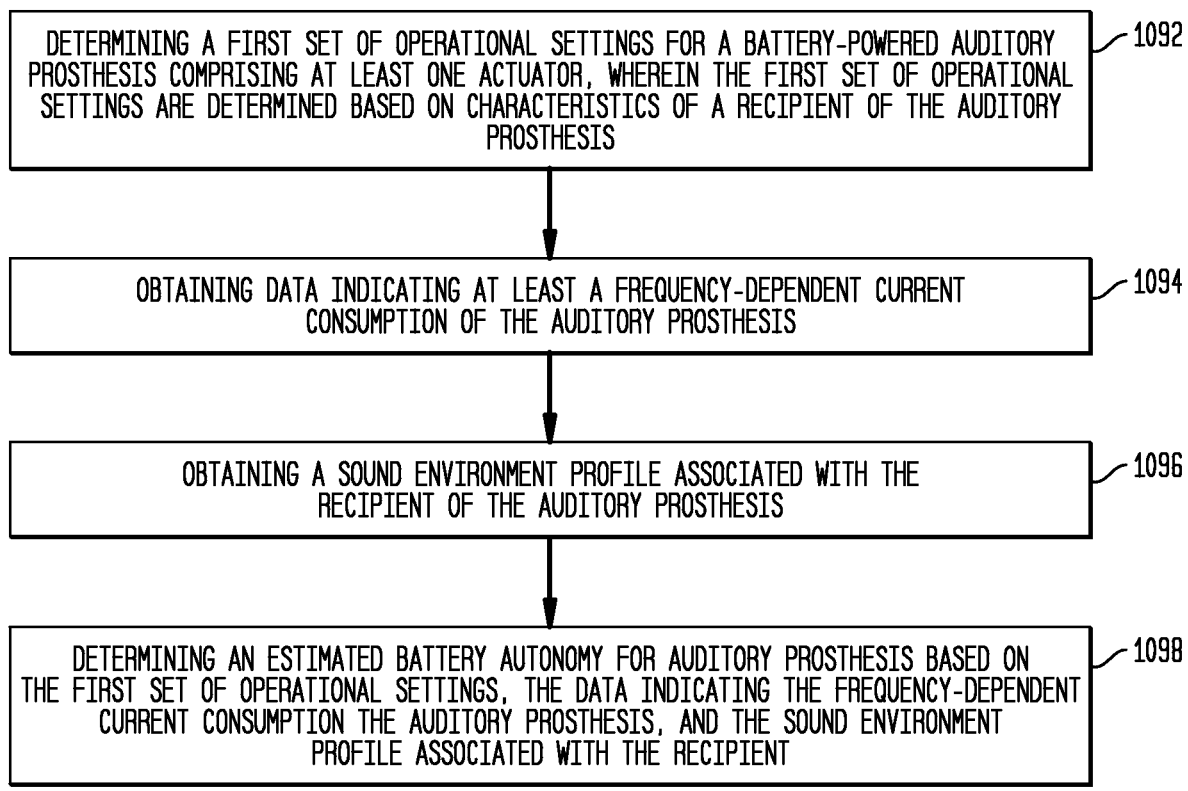
FIG. 10 is a flowchart of another method, in accordance with certain embodiments presented herein.

FIG. 10 is a flowchart of a method 1090 in accordance with certain embodiments presented herein. Method 1090 begins at 1092 where a computing device determines a first set of operational settings for a battery-powered auditory prosthesis comprising at least one actuator. The first set of operational settings are determined based on characteristics of a recipient of the auditory prosthesis. At 1094, the computing device obtains data indicating at least a frequency-dependent current consumption of the auditory prosthesis. At 1096, the computing device obtains a sound environment profile associated with the recipient of the auditory prosthesis. At 1098, the computing device determines an estimated battery autonomy for the auditory prosthesis based on the first set of operational settings, the data indicating the frequency-dependent current consumption the auditory prosthesis, and the sound environment profile associated with the recipient.

It is to be appreciated that the embodiments presented herein are not mutually exclusive and that the various embodiments may be combined with another in any of a number of different manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
obtaining a hearing prescription associated with a recipient of a mechanically-stimulating auditory prosthesis, wherein the mechanically-stimulating auditory prosthesis is configured to be powered by at least one battery; and
determining, based on the hearing prescription and a frequency-level current consumption of the mechanically-stimulating auditory prosthesis, an estimated battery autonomy of the mechanically-stimulating auditory prosthesis.

2. The method of claim 1, further comprising:
configuring the mechanically-stimulating auditory prosthesis based on the estimated battery autonomy.

3. The method of claim 1, further comprising:
obtaining data indicative of a hearing loss of the recipient; and
generating the hearing prescription of the recipient based on the data indicative of the hearing loss of the recipient.

4. The method of claim 3, wherein obtaining data indicative of a hearing loss of the recipient comprises:
obtaining an audiogram of hearing loss of at least a first ear of the recipient.

5. The method of claim 1, further comprising:
determining whether the estimated battery autonomy is appropriate for the recipient.

6. The method of claim 5, wherein determining whether the estimated battery autonomy is appropriate for the recipient comprises:
determining whether the estimated battery autonomy is greater than a first time threshold.

7. The method of claim 6, wherein determining whether the estimated battery autonomy is appropriate for the recipient further comprises:
determining whether the estimated battery autonomy is less than a second time threshold.

8. The method of claim 5, wherein the estimated battery autonomy is determined to be inappropriate for the recipient, and wherein the method comprises:
determining, based on the estimated battery autonomy, an adjusted hearing prescription associated with the recipient.

9. The method of claim 8, further comprising:
determining, based on the adjusted hearing prescription associated with the recipient and the frequency-level current consumption of the mechanically-stimulating auditory prosthesis, an adjusted estimated battery autonomy of the mechanically-stimulating auditory prosthesis.

10. The method of claim 8, wherein the determining the adjusted hearing prescription associated with the recipient comprises:
adjusting one or more frequency-dependent gain settings of the mechanically-stimulating auditory prosthesis.

11. The method of claim 1, further comprising:
determining a sound environment profile for the recipient; and
determining the estimated battery autonomy based on the hearing prescription, the frequency-level current consumption of the mechanically-stimulating auditory prosthesis, and the sound environment profile for the recipient.

12. The method of claim 11, further comprising:
obtaining prior recipient data associated with other recipients of other mechanically-stimulating auditory prostheses; and
determining the estimated battery autonomy based on the hearing prescription, the frequency-level current consumption of the mechanically-stimulating auditory prosthesis, the sound environment profile for the recipient, and the prior recipient data.

13. The method of claim 12, further comprising:
logging, over a period of time, recipient data associated with the recipient's use of the mechanically-stimulating auditory prosthesis during the period of time;
determining, based on the logged recipient data, a refined sound environment profile for the recipient; and
determining an adjusted estimated battery autonomy based on the hearing prescription, the frequency-level current consumption of the mechanically-stimulating auditory prosthesis, and the refined sound environment profile.

14. The method of claim 13, further comprising:
programming the mechanically-stimulating auditory prosthesis based on the adjusted estimated battery autonomy.

15. One or more non-transitory computer readable storage media comprising instructions that, when executed by at least one processor, are operable to:
obtain a first set of operational settings of a battery-powered medical device having at least one actuator, wherein the first set of operational settings are determined based on characteristics of a recipient of the medical device;
obtain data indicating at least a frequency-dependent current consumption of the at least one actuator; and
predict, based on the data indicating the frequency-dependent current consumption of the at least one actuator, an estimated run-time of the medical device when operated in accordance with the first set of operational settings.

16. The one or more non-transitory computer readable storage media of claim 15, further comprising instructions operable to:
obtain data indicating a level-dependent current consumption of the at least one actuator; and
predict the estimated run-time of the medical device when operated in accordance with the first set of operational settings based on the data indicating the frequency-dependent current consumption of the at least one actuator and the data indicating a level-dependent current consumption of the at least one actuator.

17. The one or more non-transitory computer readable storage media of claim 15, wherein the medical device is an auditory prosthesis, and wherein the one or more non-transitory computer readable storage media further comprise instructions operable to:
obtain data indicative of a hearing loss of the recipient; and
determine the first set of operational settings based on the data indicative of the hearing loss of the recipient.

18. The one or more non-transitory computer readable storage media of claim 15, further comprising instructions operable to:
  determine whether the estimated run-time is appropriate for the recipient.

19. The one or more non-transitory computer readable storage media of claim 18, wherein the instructions operable to determine whether the estimated run-time is appropriate for the recipient comprise instructions operable to:
  determine whether the run-time is greater than a first time threshold.

20. The one or more non-transitory computer readable storage media of claim 19, wherein the instructions operable to determine whether the estimated run-time is appropriate for the recipient comprise instructions operable to:
  determining whether the run-time is less than a second time threshold.

21. The one or more non-transitory computer readable storage media of claim 18, wherein the estimated run-time is determined to be appropriate for the recipient, and wherein the one or more non-transitory computer readable storage media further comprise instructions operable to:
  configure the medical device based on the estimated run-time.

22. The one or more non-transitory computer readable storage media of claim 18, wherein the estimated run-time is determined to be inappropriate for the recipient, and wherein the one or more non-transitory computer readable storage media further comprise instructions operable to:
  determining, based on the estimated run-time, a second set of operational settings for the medical device; and
  predict, based on the data indicating the frequency-dependent current consumption of the at least one actuator, an adjusted estimated run-time of the medical device when operated in accordance with the second set of operational settings.

23. The one or more non-transitory computer readable storage media of claim 22, wherein the instructions operable to determine the second set of operational settings for the medical device comprise instructions operable to:
  adjust one or more frequency-dependent gain settings of the medical device between the first set of operational settings and the second set of operational settings.

24. The one or more non-transitory computer readable storage media of claim 15, further comprising instructions operable to:
  obtain an environmental profile of the recipient; and
  predict the estimated run-time of the medical device when operated in accordance with the first set of operational settings based on the data indicating the frequency-dependent current consumption of the at least one actuator and the environmental profile of the recipient.

25. The one or more non-transitory computer readable storage media of claim 24, wherein the environmental profile of the recipient is a sound environment profile of the recipient.

26. The one or more non-transitory computer readable storage media of claim 24, further comprising instructions operable to:
  obtain prior recipient data associated with other recipients of other medical devices; and
  predict the estimated run-time of the medical device when operated in accordance with the first set of operational settings based on the data indicating the frequency-dependent current consumption of the at least one actuator, the environmental profile of the recipient, and the prior recipient data.

* * * * *